(12) United States Patent
Mitsuhashi et al.

(10) Patent No.: US 10,697,001 B2
(45) Date of Patent: Jun. 30, 2020

(54) DEVICES AND METHODS FOR CAPTURING TARGET MOLECULES

(71) Applicants: HITACHI CHEMICAL CO., LTD., Tokyo (JP); HITACHI CHEMICAL CO. AMERICA, LTD., San Jose, CA (US)

(72) Inventors: Masato Mitsuhashi, Irvine, CA (US); Taku Murakami, Irvine, CA (US)

(73) Assignees: HITACHI CHEMICAL CO., LTD., Tokyo (JP); HITACHI CHEMICAL CO. AMERICA, LTD., San Jose, CA (US)

( * ) Notice: Subject to any disclaimer, the term of this patent is extended or adjusted under 35 U.S.C. 154(b) by 0 days.

(21) Appl. No.: 15/456,236

(22) Filed: Mar. 10, 2017

(65) Prior Publication Data

US 2017/0247744 A1    Aug. 31, 2017

Related U.S. Application Data

(63) Continuation of application No. 14/889,131, filed as application No. PCT/US2013/063114 on Oct. 2, 2013, now Pat. No. 9,662,649.

(Continued)

(51) Int. Cl.
*C12Q 1/6806* (2018.01)
*B04B 3/00* (2006.01)
(Continued)

(52) U.S. Cl.
CPC .......... *C12Q 1/6806* (2013.01); *B01L 3/502* (2013.01); *B01L 3/5021* (2013.01); *B04B 3/00* (2013.01);
(Continued)

(58) Field of Classification Search
CPC ........ G01N 1/18; G01N 1/405; G01N 1/4077; B04B 3/00; B01L 3/502; B01L 3/5021; C12Q 1/6806
(Continued)

(56) References Cited

U.S. PATENT DOCUMENTS

| 3,583,627 A | 6/1971 | Wilson |
| 4,895,706 A | 1/1990 | Root et al. |

(Continued)

FOREIGN PATENT DOCUMENTS

| EP | 0 588 564 | 3/1994 |
| EP | 1 672 062 | 6/2006 |

(Continued)

OTHER PUBLICATIONS

"Binding Assays with Membranes," Jan. 1, 2006, Protein Biochemistry and Protoeomics, Elsevier, pp. 37-39.

(Continued)

*Primary Examiner* — Brian J. Sines
(74) *Attorney, Agent, or Firm* — Knobbe Martens Olson & Bear LLP

(57) ABSTRACT

Provided herein are devices and methods for the capture or isolation of a biomarker from a biological sample. In several embodiments, the device comprises a loading region, a filter material, and a receiving region. In particular, in several embodiments, biological fluid is passed from the loading region through the filter material and into the receiving region, thereby resulting in capture or isolation of a biomarker.

13 Claims, 12 Drawing Sheets

Related U.S. Application Data

(60) Provisional application No. 61/820,110, filed on May 6, 2013.

(51) Int. Cl.
    *B01L 3/00* (2006.01)
    *G01N 1/40* (2006.01)

(52) U.S. Cl.
    CPC .......... *G01N 1/405* (2013.01); *G01N 1/4077* (2013.01); *B01L 3/50255* (2013.01); *B01L 2200/025* (2013.01); *B01L 2200/026* (2013.01); *B01L 2200/028* (2013.01); *B01L 2300/021* (2013.01); *B01L 2300/0681* (2013.01); *B01L 2300/0829* (2013.01); *B01L 2400/0409* (2013.01); *G01N 2001/4088* (2013.01)

(58) Field of Classification Search
    USPC .............................. 436/174, 175, 177, 178
    See application file for complete search history.

(56) References Cited

U.S. PATENT DOCUMENTS

| | | | |
|---|---|---|---|
| 4,925,572 A | 5/1990 | Pall | |
| 5,139,685 A | 8/1992 | de Castro et al. | |
| 5,372,945 A | 12/1994 | Alchas et al. | |
| 5,589,568 A * | 12/1996 | Higashijima | C07K 14/43568 530/324 |
| 5,647,990 A | 7/1997 | Vassarotti | |
| 5,733,449 A | 3/1998 | Bowers et al. | |
| 5,747,256 A | 5/1998 | Yan et al. | |
| 6,007,498 A | 12/1999 | Buck et al. | |
| 6,329,179 B1 | 12/2001 | Kopreski | |
| 6,344,345 B1 | 2/2002 | Hayashizaki | |
| 6,375,855 B1 | 4/2002 | Vassarotti | |
| 6,964,850 B2 | 11/2005 | Bevilacqua et al. | |
| 7,026,121 B1 | 4/2006 | Wohlgemuth et al. | |
| 7,608,402 B2 | 10/2009 | Li et al. | |
| 7,741,023 B2 | 6/2010 | Mitsuhashi | |
| 7,745,180 B2 | 6/2010 | Mitsuhashi | |
| 8,567,609 B2 | 10/2013 | Landrigan et al. | |
| 8,591,391 B2 | 11/2013 | Chavarria et al. | |
| 9,012,615 B2 | 4/2015 | Mitsuhashi et al. | |
| 9,458,496 B2 | 10/2016 | Mitsuhashi et al. | |
| 10,266,895 B2 | 4/2019 | Mitsuhashi et al. | |
| 2002/0011450 A1 | 1/2002 | Kelly et al. | |
| 2002/0146696 A1 | 10/2002 | Burgoyne et al. | |
| 2003/0036077 A1 | 2/2003 | Chenchik | |
| 2003/0203453 A1 | 10/2003 | Leonard | |
| 2004/0029124 A1 | 2/2004 | Zohlnhofer et al. | |
| 2004/0072193 A1 | 4/2004 | Mitsuhashi | |
| 2004/0203037 A1 | 10/2004 | Lo et al. | |
| 2004/0258570 A1 | 12/2004 | Beebe et al. | |
| 2004/0265864 A1 | 12/2004 | Mitsuhashi | |
| 2005/0064472 A1 | 3/2005 | Shekar et al. | |
| 2006/0008804 A1 | 1/2006 | Chibout et al. | |
| 2006/0144790 A1 | 7/2006 | Kelly et al. | |
| 2007/0196871 A1 | 8/2007 | Reich | |
| 2007/0254351 A1 | 11/2007 | Abrignani et al. | |
| 2007/0264272 A1 | 11/2007 | Perreault et al. | |
| 2008/0009009 A1 | 1/2008 | Mitsuhashi | |
| 2008/0015162 A1 | 1/2008 | Bhanot et al. | |
| 2008/0025967 A1 | 1/2008 | Doi et al. | |
| 2008/0299558 A1 | 4/2008 | Kondo et al. | |
| 2008/0188816 A1 | 8/2008 | Shimazaki et al. | |
| 2008/0233573 A1 | 9/2008 | Storm et al. | |
| 2008/0268429 A1 | 10/2008 | Pietrzkowski | |
| 2009/0011410 A1 | 1/2009 | Mitsuhashi | |
| 2009/0023149 A1 | 1/2009 | Knudsen | |
| 2009/0149333 A1 | 6/2009 | Knudsen et al. | |
| 2009/0258379 A1 | 10/2009 | Klein et al. | |
| 2010/0027315 A1 | 2/2010 | Kim | |
| 2010/0113290 A1 | 5/2010 | Klass et al. | |
| 2010/0184046 A1 | 7/2010 | Klass et al. | |
| 2010/0196426 A1 | 8/2010 | Skog | |
| 2010/0203529 A1 | 8/2010 | Kuslich et al. | |
| 2010/0216131 A1 | 8/2010 | Luthra et al. | |
| 2010/0143898 A1 | 10/2010 | Kutyavin | |
| 2011/0143348 A1 | 6/2011 | Tomigahara et al. | |
| 2011/0171647 A1 | 7/2011 | Tomigahara et al. | |
| 2011/0189674 A1 | 8/2011 | Tomigahara et al. | |
| 2011/0195426 A1 | 8/2011 | Russo | |
| 2011/0223583 A1 | 9/2011 | Gordon et al. | |
| 2011/0287964 A1 | 11/2011 | Bonventre et al. | |
| 2012/0211566 A1 | 8/2012 | Hensel et al. | |
| 2012/0264628 A1 | 10/2012 | Okamoto et al. | |
| 2013/0089855 A1 * | 4/2013 | Mitsuhashi | C12Q 1/6883 435/5 |
| 2013/0089864 A1 * | 4/2013 | Mitsuhashi | C12Q 1/6809 435/6.11 |
| 2013/0123124 A1 | 5/2013 | Kunkel | |
| 2013/0165338 A1 | 6/2013 | Schmidt-Ott et al. | |
| 2013/0172208 A1 | 7/2013 | Mitsuhashi | |
| 2013/0197514 A1 | 8/2013 | Jiang | |
| 2013/0323751 A1 | 12/2013 | Singbartl et al. | |
| 2013/0337462 A1 | 12/2013 | Mergemeier | |
| 2014/0099649 A1 | 4/2014 | Mitsuhashi | |
| 2014/0141986 A1 * | 5/2014 | Spetzler | C12Q 1/6886 506/9 |
| 2014/0148348 A1 * | 5/2014 | Kuslich | C12Q 1/6886 506/7 |
| 2014/0148350 A1 * | 5/2014 | Spetzler | G01N 33/574 506/9 |
| 2014/0194613 A1 | 7/2014 | Skog et al. | |
| 2015/0141634 A1 | 5/2015 | Mitsuhashi | |
| 2015/0275301 A1 | 10/2015 | Mitsuhashi et al. | |
| 2015/0301055 A1 | 10/2015 | Spetzler | |
| 2016/0074860 A1 | 3/2016 | Mitsuhashi | |
| 2016/0122823 A1 | 5/2016 | Mitsuhashi | |
| 2016/0222456 A1 | 8/2016 | Yamamoto | |
| 2016/0237496 A1 | 8/2016 | Mitsuhashi | |
| 2017/0184575 A1 | 6/2017 | Murakami | |
| 2017/0283789 A1 | 10/2017 | Yamamoto | |
| 2017/0335397 A1 | 11/2017 | RamachandraRao et al. | |
| 2018/0265914 A1 | 9/2018 | Murakami | |
| 2018/0327852 A1 | 11/2018 | Murakami | |

FOREIGN PATENT DOCUMENTS

| | | |
|---|---|---|
| JP | S50-76284 | 6/1975 |
| JP | S58-159420 | 9/1983 |
| JP | S59-225195 | 12/1984 |
| JP | 1997-067336 | 3/1997 |
| JP | 2003-530854 | 10/2003 |
| JP | 2007-181440 | 7/2007 |
| JP | 2008-005840 | 1/2008 |
| JP | 2008-151517 | 7/2008 |
| JP | 2012-185173 | 9/2012 |
| JP | 2013-000107 | 1/2013 |
| JP | 2014-035186 | 2/2014 |
| WO | WO 1993/19831 | 10/1993 |
| WO | WO 2001/051170 | 7/2001 |
| WO | WO 2001/079486 | 10/2001 |
| WO | WO 2002/057414 | 7/2002 |
| WO | WO 2006/010464 | 2/2006 |
| WO | WO 2006/045053 | 4/2006 |
| WO | WO 2008/092993 | 8/2008 |
| WO | WO 2009/015357 | 1/2009 |
| WO | WO 2009/057695 | 5/2009 |
| WO | WO 2009/070442 | 6/2009 |
| WO | WO 2009/100029 | 8/2009 |
| WO | WO 2009/120561 | 10/2009 |
| WO | WO 2010/056337 | 5/2010 |
| WO | WO 2010/086163 | 8/2010 |
| WO | WO 2011/031892 | 3/2011 |
| WO | WO 2011/054893 | 5/2011 |
| WO | WO 2011/084333 | 7/2011 |
| WO | WO 2011/100458 | 8/2011 |
| WO | WO 2011/112961 | 9/2011 |
| WO | WO 2011/127219 | 10/2011 |
| WO | WO 2011/156734 | 12/2011 |

(56) References Cited

FOREIGN PATENT DOCUMENTS

| WO | WO 2011/156763 | 12/2011 |
|---|---|---|
| WO | WO 2012/057498 | 5/2012 |
| WO | WO 2012/102963 | 8/2012 |
| WO | WO 2012/125470 | 9/2012 |
| WO | WO 2012/170037 | 12/2012 |
| WO | WO 2013/012947 | 1/2013 |
| WO | WO 2013/028788 | 2/2013 |
| WO | WO 2013/041913 | 3/2013 |
| WO | WO 2013/043922 | 3/2013 |
| WO | WO 2013/134786 | 9/2013 |
| WO | WO 2013/188846 | 12/2013 |
| WO | WO 2013/192616 | 12/2013 |
| WO | WO 2014/021125 | 2/2014 |
| WO | WO 2014/055687 | 4/2014 |
| WO | WO 2014/130825 | 8/2014 |
| WO | WO 2014/182330 | 11/2014 |
| WO | WO 2015/021158 | 2/2015 |
| WO | WO 2015/050891 | 4/2015 |
| WO | WO 2015/082372 | 6/2015 |
| WO | WO 2015/179773 | 11/2015 |
| WO | WO 2016/033287 | 3/2016 |
| WO | WO 2016/077537 | 5/2016 |
| WO | WO 2017/040515 | 3/2017 |
| WO | WO 2017/040520 | 3/2017 |

OTHER PUBLICATIONS

Anonymous: "ExoMir Kit Manual Catalog #5145," Bio Scientific. XP002736098.
Arteaga et al., Endothelial microparticles and platelet and leukocyte activation in pateints with the metabolic symdrome, Am J Cardiol, vol. 98:70-74 (2006).
Bachmann et al., Renal effects of Tamm-Horsfall protein (uromodulin) deficiency in mice, Am J Physiol, Renal Physiol, 288:F559-567 (2005).
Barnett et al., Angiotensin-Receptor Blockade versus Converting-Enzyme Inhibition in Type 2 Diabetes and Nephropathy, N Eng J Med (2004) 351:1952-61.
Beltrami, et al.: "Analysis of urinary microRNAs in chronic kidney disease: Figure1," Biochemical Society Transactions, vol. 12, No. 4, Aug. 1, 2012, pp. 4-879.
Bio Scientific, "ExoMir Kit Manual", Catalog 5145, www.yumpu.com/en/document/view/30138118/exomirtm-kit-manual-nordic-biosite/2, Feb. 17, 2015.
Chen et al., Microfluidic isolation and transcriptome analysis of serum microvesicles, J Royal Soc of Chem (2010) vol. 10:505-511.
Cheruvanky et al.: Rapid isolation of urinary exosomal biomarkers using a namomembrane ultrafiltration concentrator, Am J. Physio. Renal. Physiol 292: F1657-F1661, 2007.
Conde-Vancells et al., Candidate biomarkers in exosome-like vesicles purified from rat and mouse urine samples, Proteomics Clin Appl 4(4):416-25 (2010).
Cutillas et al., The urinary proteome in Fanconi syndrome implies specificity in the reabsorption of proteins by renal proximal tubule cells, Am J Physio Renal Physiol (2004) vol. 287(3):353-364.
Dennis et al., Identification from public data of molecular markers of adenocarcinoma characteristic of the site of origin, Cancer Res, vol. 62(21):5999-6005 (2002).
Enard et al., Intra- and Interspecific Variation in Primate Gene Expression Patterns, Science (2002) vol. 296:340.
Erusalimsky et al.: A Glass Fiber/Diethylaminoethyl Double Filter Binding Assay That Measures Apoptotic Internucleosomal DNA Fragmentation, Analytical Biochemistry 242, 187-196 (1996) Article No. 0452.
Ferguson et al.: Vesicular Localization and Activity-Dependent Trafficking of Presynaptic Choline Transponders, The Journal of Neuroscience, Oct. 29, 2003, 23(30):9697-9699.
Ferguson et al.: Vesicular Localization and Activity-Dependent Trafficking of Presynaptic Choline Transponders, The Journal of Neuroscience, Oct. 29, 2003, 23(30):9697-9709.

Gene Cards DEFA3 Gene, first internet archive Aug. 7, 2010, pp. 1-14.
Golub, et al.: "Molecular Classification of Cancer: Class Discovery and Class Prediction by Gene Expression Monitoring," Science, vol. 286, pp. 531-537, Oct. 1999.
Gonzales et al., Large-scale proteomics and phosphoproteomics of urinary exosomes, J Am Soc Nephrol, 20(2):363-79 (2009).
Guo et al., Surfactant protein gene A, B, and D marker alleles in chronic obstructive pulmonary disease of a Mexican population, Eur Respir J, 18(3):482-90 (2001).
Haas et al., Patient characteristics associated with successful mobilizing and autografting of peripheral blood progenitor cells in malignant lymphoma, Blood (1994) vol. 83(12):3787-3794.
Harada and Mitsuhashi, "Assessment of post-transplant kidney function by measuring glomerulus and tubule specific mRNAs in urine exosome," American Journal of Transplantation, vol. 12, Supp. 3, pp. 369-370, Abstract No. 1158, May 2012.
Hashem, Biochemical and expression studies on Acquaporin 9 (AQP9) in wild and AQP9 knockout mice, Veterinarski Archiv (2010) vol. 80(1):93-112.
Hewitt et al., Discovery of Protein Biomarkers for Renal Diseases, J Am Soc Nephrol (2004) vol. 15(7):1677-1689.
Hoorn et al., Prospects for urinary proteomics: exosomes as a source of urinary biomarkers, Nephrology, 10:283-290 (2005).
Hotfilder et al., Def-2, -3, -6 and -8, novel mouse genes differentially expressed in the haemopoietic system, Brit J Haematol (1999) vol. 106:335-344.
Hunter et al., Detection of microRNA expression in human peripheral blood microvesicles, PLoS One 3:e3694 (2008).
Ito et al., Myeloid Reconstruction. Serum stem cell growth factor for monitoring hematopoietic recovery following stem cell transplantation, Bone Marrow Transplantation (2003) vol. 32:391-398.
Jimenez et al., Endothelial microparticles released in thrombotic thrombocytopenic purpura express von Willibrand factor and markers of endothelial activation, Br J Haemat (2003) vol. 123(5):896-902.
Keller et al., "Body fluid derived exosomes as a novel template for clinical diagnostics," Journal of Translational Medicine, vol. 9, 86, Jun. 2011, printed as pp. 1/9-9/9.
Klein et al., Ex-Vivo Assessment of Candidate Anti-Inflammatory Agents in the Treatment of Gram Negative Sepsis, Immun & Infec Dis (1994) vol. 4(1):33-35.
Koga et al., Purification, characterization and biological significance of tumor-derived exosomes, Anticancer Res, 25(6A):3703-7 (2005).
Labsource: Whatman Glass Microfiber Filters, printed from internet Dec. 12, 2009 2011:<URL:http://www.labsource.com/Catalog/Group.aspx?GroupID=82>] p. 1.
Lescuyer et al., Proteomics: Clinical Applications (2008) vol. 2(7-8):1008.
Lucendo et al., Treatment with topical steroids downregulates IL-5, eotaxin-1/CCL11, and eotaxin-3/CCL26 gene expression in eosinophilic esophagitis, Am J Gastro 103(9):2184-93 (2008).
Luo et al., RANTES stimulates inflammatory cascades and receptor modulation in murine astrocytes, 39(1):19-30 (2002).
Mathivanan, et al.: "ExoCarta 2012: database of exosomal proteins, RNA and lipids," Nucleic Acids Research, vol. 40, No. D1, Oct. 11, 2011, pp. D1241-D1244.
Mathivanan, et al.: "Exosomes: Extracellular Organelles Important in Intercellular Communication," J of Proteomics 73(10)1907-20, 2010.
Miranda et al., Nucleic acids within urinary exosomes/microvesicles are potential biomarkers for renal disease, Kidney Intl (2010) vol. 78(2):191-199.
Mitchell et al., Can urinary exosomes act as treatment response markers in prostate cancer? J Transl Med, 12:7:4 (2009).
Muller, Gunter: "Microvesicles/exosomes as potential novel biomarkers of metabolic diseases," Diabetes, Metabolic Syndrom and Obesity: Targets and Therapy, Aug. 1, 2012, p. 247.
Murakami et al.: "Development of Glomerulus-, Tubuel-, and Collecting Duct-Specific mRNA Assay in Human Urinary Exosomes and Microvesicles," PLoS One vol. 9, Oct. 2014, pp. 1-10.

(56) References Cited

OTHER PUBLICATIONS

Nilsson et al., Prostate cancer-derived urine exosomes: a novel approach to biomarkers for prostate cancer, Br J Cancer 100:1603-1607 (2009).
Notterman et al., in Microarrays and Cancer Research (2002) Warrington et al. (eds.) pp. 81-111 at pp. 81-82.
Olszewska-Pazdrak et al., Cell-specific expression of RANTES, MCP-1, and MIP-1 alpha by lower airway epithelial cells and eosinophils infected with respiratory syncytial virus, J Virol, 72(6):4756-64 (1998).
Pisitkun et al., Discovery of urinary biomarkers, Mol Cell Proteomics, 5(10):1760-71 (2006).
Pisitkun et al., Identification and proteomic profiling of exosomes in human urine, Proc Natl Acad Sci USA, 101:13368-73 (2004).
Post et al., Demonstration of the presence of independent pre-osteoblastic and pre-adipocytic cell populations in bone marrow-derived mesenchymal stem cells, Bone, 43(1):32-9 (2008).
Pusztai et al.: "Clinical trial design for microarray predictive marker discovery and assessment," Annals of Oncology 15: 1731-1737, 2004.
Rappa et al., The stem cell-associated antigen CD133 (Prominin-1) is a molecular therapeutic target for metastatic melanoma, Stem Cells, 26:3008-17 (2008).
Rehm, Hubert: "Binding Assays with Membranes", 2.2 Binding, Protein Biochemistry and Proteomics, Elesevier, pp. 37-39.
Sartorius Stedim Biotech., Ultrafiltration & Protein Purification Products. Fisher Scientic, pp. 1-96, Mar. 2011.
Sellam et al., Increased levels of circulating microparticles in primary Sjögren's syndrome, systemic lupus erythematosus and rheumatoid arthritis and relation with disease activity, Arthritis Res Ther 11(5):R156 (2009).
Simpson et al., Proteomic profiling of exosomes: current perspectives, Proteomics 8(19):4083-99 (2008).
Smalley et al., Isolation and identification of potential urinary microparticle biomarkers of bladder cancer, J Proteome Res 7:2088-96 (2008).
Strausberg et al., Reading the Molecular Signatures of Cancer, Microarrays & Cancer Res (2002) pp. xi-xvi.
Taylor et al., MicroRNA signatures of tumor-derived exosomes as diagnostic biomarkers of ovarian cancer, Gynecol Oncol 110(1):13-21 (2008).
Thery et al., Isolation and characterization of exosomes from cell culture supernatants and biological fluids, Chapter 3, Curr Protoc Cell Biol, Unit 3.22 (2006).
Tockman et al., Considerations in bringing a cancer biomarker to clinical application, Cancer Res 1:52(9Suppl):2711s-2718s (1992).
Tomblyn et al., Guidelines for preventing infectious complications among hematopoietic cell transplantation recipients: A global prespective, Biol Blood Marrow Trans (2009) vol. 15:1143-1238.
Vaes et al., Comprehensive microarray analysis of bone morphogenetic protein 2-induced osteoblast differentiation resulting in the identification of novel markers for bone development, J Bone Miner Res 17(12):2106-18 (2002).
Van Niel et al., Exosomes: a common pathway for a specialized function, J Biochem 140(1):13-21 (2006).
Van't Veer et al., Enabling personalized cancer medicine through analysis of gene-expression patterns, Nature 452(7187):564-70 (2008).
Wellmann et al., Detection of differentially expressed genes in lymphomas using cDNA arrays: identification of clusterin as a new diagnostic marker for anaplastic large-cell lymphomas, Blood (2000) vol. 96(2):398-404.
Whitehead et al., Variation in tissue-specific gene expression among natural populations, Genome Biol 6(2):R13 (2005).
Xu et al., Gene expression in peripheral blood differs after cardioembolic compared with large-vessel atherosclerotic stroke: biomarkers for the etiology of ischemic stroke, JCBFM (2008) vol. 28:1320-1328.
Zefon International. Glass Fiber Filters, Jan. 14, 2010 (printed from internet Oct. 7, 2011) <http://web.archive.org/web/20100114112921/http://www.zefon.com/store/glass-fiber-filters/>].

Zheng et al., Urinary Podocyte-Associated mRNA profile in Various Stages of Diabetic Nephropathy, PLoS one (2011) vol. 6(5):1-7.
Zhou et al., Urinary exosomal transcription factors, a new class of biomarkers for renal disease, Kidney Intl (2008) vol. 74(5):613-621.
Zucker et al., Immature platelet fraction as a predictor of platelet recovery following hematopoietic progenitor cell transplantation, Lab Hematol (2006) vol. 12:125-130.
Jan. 5, 2012 ISR/WO from related PCT App No. PCT/US2011/40015.
Dec. 27, 2012 IPRP from related PCT App No. PCT/US2011/40015.
Aug. 19, 2014 Office Action from related JP App No. 2013-514399.
Oct. 21, 2011 ISR/WO from related PCT App No. PCT/US2011/040057.
Sep. 26, 2014 Office Action from related U.S. Appl. No. 14/122,920.
Mar. 9, 2015 European Partial Supplementary Search Report, re 11867123.9 (PCT/US2011040076).
Dec. 10, 2013 IPRP/WO from related PCT App No. PCT/US2011/040076.
Jan. 10, 2012 ISR/WO from related PCT App No. PCT/US2011/40076.
Japanese Office Action (Notice of Reason for Rejection) re JP Application No. 2014-51443, dated May 19, 2015.
Jan. 17, 2014 ISR/WO from related PCT App No. PCT/US13/63122.
Jan. 29, 2015 IPRP from related PCT App No. PCT/US13/63122.
Mar. 11, 2014 ISR/WO from related PCT App No. PCT/US2013/063114.
Nov. 10, 2015 ISR/WO from related PCT App No. PCT/US2013/063114.
Mar. 19, 2015 International Search Report with Written Opinion for PCT/US14/58404 filed Sep. 30, 2014 (24 pages).
Absolute Quantitation Using Standard Curve Getting Guide, Applied Biosystems, pp. i-viii and 1-80, Jun. 2010, printed from http://www3.appliedbiosystems.com/cms/groups/mcb_support/documents/generaldocuments/cms_032176.pdf.
Anglicheau et al., "Discovery and Validation of a Molecular Signature for the Noninvasive Diagnosis of Human Renal Allograft Fibrosis," NIH Public Access, Author Manuscript, Transplantation Jun. 15, 2012; 93(11): 1136-1146.
Bakris, GL., Recognition, pathogenesis, and treatment of different stages of nephropathy in patients with type 2 diabetes mellitus. Mayo Clinc Proceedings, vol. 86, No. 5, pp. 444-456, May 2011.
Chen et al., Inhibition of Ultraviolet B-Induced c-fos Gene Expression and p38 Mitogen-Activated Protein Kinase Activation by (−)-Epigallocatechin Gallate in a Human Keratinocyle Cell Line, Molecular Carcinogenesis (1999) vol. 24(2):79-84.
Duffield et al. Simultaneous determination of multiple mRNA levels utilizing MALDI-TOF mass spectrometry and biotinylted dideoxynucleotides. RNA, vol. 16, pp. 1285-1291, (2010).
Fuchs et al., "An Exploratory Evaluation of the Utility of Transcriptional and Urnary Kidney Injury Biomarkers for the Prediction of Aristolochic Acid-Induced Renal Injury in Male Rates," Veterinary Pathology, 2014, vol. 51 (3) 680-694.
Gallagher et al. "Unit 10.8: Immunoblotting and Immunodetection" in Current Protocols in Molecular Biology, Supplement 66, pp. 10.8.1-10.8.24, (2004).
Gonzales et al., Chapter 6: Isolation and Purification of Exosomes in Urine in Alex J. Rai (ed.), The Urinary Proteome: Methods and Protocols, Methods in Molecular Biology, vol. 641, pp. 89-99, 2010.
Grant et al., A filtration-based protocol to isolate human plasma membrane-derived viscles and exosomes from blood plasma. Journal of Immunocological Methods, vol. 371,pp. 143-151, Jun. 30, 2011.
Hess et al., The hydroxylamine of sulfamethoxazole synergizes with FK506 and cyclosporin A, inhibiting T-Cell proliferation, J Pharm & Exp Tech (1996) vol. 281(1):540-548.
Hornbeck, et al., "Unit 11.2: Enzyme-Linked Immunosorbent Assays (ELISA)" in Current Protocols in Biology, Supplement 15, pp. 11.2.1-11.2.22, (1991).
Ide et al., "Transduction of Murine Hematopoietic Stem Cells and In Vivo Selection of Gene-Modified Cells," Methods in Molecular Biology, vol. 433,: vol. 1: Production and In Vivo Applications of Gene Transfer Vectors, 2008, pp. 213-228.

(56) References Cited

OTHER PUBLICATIONS

Liu et al., Transcriptome profiling and sequencing of differentiated human hematopoietic stem cells reveal lineage-specific expression and alternative splicing of genes, Physiol Genomics 43:1117-1134, 2011.
Lu et al., "Tracking single hematopoietic stem cells in vivo using high-throughput sequencing in conjunction with viral genetic barcoding," Nature Biotechnology 29, 928-933 (2011) and supplementary data.
Patterson, SD. "Unit 10.22: Protein Identification and Characterization by Mass Spectrometry" in Current Protocols in Molecular Biology, Supplement 41, pp. 10.22.1-10.22.24, (1998).
Stahlberg et al., Properties of the reverse transcription reaction in mRNA quantification. Clinical Chemistry, vol. 50, No. 3, pp. 509-515, 2004.
Tjiong et al., "Increased IL-6 and IL-8 levels in cervicovaginal secretions of paitents with cervical cancer," Gynecol. Oncol. May 1999, vol. 73, No. 2, pp. 285-291.
Alvarez ML, et al., Comparison of protein, microRNA, and mRNA yields using different methods of urinary exosome isolation for the discovery of kidney disease biomarkers. Kidney Int. 82: 1024-1032, 2012.
Anders S, et al., Count-based differential expression analysis of RNA sequencing data using R and Bioconductor. Nat. Protoc. 8: 1765-1786, 2013.
Ayodele et al., 'Diabetic Nephropathy—A review of the natural history, burden, risk factors and treatment,' Journal of the National Medical Association, vol. 96, No. 11, pp. 1445-1454, Nov. 2004.
Bailey et al., "Transplanted adult hematopoietic stems cells differentiate into functional endothelial cells," The American Society of Hematology, Plenary paper, 2004.
Baldi P, et al., A Bayesian framework for the analysis of microarray expression data: regularized t—test and statistical inferences of gene changes. Bioinformatics 17: 509-519, 2001.
Botteman MF, et al., The health economics of bladder cancer: a comprehensive review of the published literature. PharmacoEconomics 21: 1315-1330, 2003.
Brushi M, et al., Glomerular Autoimmune Multicomponents of Human Lupus Nephritis In Vivo: $\alpha$-Enolase and Annexin Al. J. Am. Soc. Nephrol. 25: 2483-2498, 2014.
Chapter 6: Transplantation, 2014 USRDS Annual Data Report, vol. 2 ESRD, pp. 153-162.
Common Cancer Types [Internet]. Natl. Cancer Inst. Available from: http://www.cancer.gov/types/common-cancers [cited Aug. 6, 2015].
Coutlee et al.,"Comparison Between Vaginal Tampon and Cervicovaginal Lavage Specimen Collection for Detection of Human Papillomavirus DNA by the Polymerase Chain Reaction," J Med Virol 51: 42-47, 1997.
DiMuccio et al., "Urinary CD133$^+$ Extracellular Vesicles Are Decreased in Kidney Transplanted Patients with Slow Graft Function and Vascular Damage," Plos One, vol. 9, No. 8, e104490, pp. 1/11-11/11, Aug. 6, 2014.
Evseenko, et al.: "Mapping the first stages of mesoderm commitment during differentiation of human embryonic stem cells," PNAS, vol. 107, No. 31, 13742-13747, Aug. 3, 2010.
Fang DY, et al., Exosomes and the kidney: Blaming the messenger. Nephrology 18: 1-10, 2013.
Feng, et al., "Research issues and strategies for genomic and proteomic biomarker discovery and validation: a statistical perspective," Pharmacogenomics, vol. 5, No. 6, pp. 709-719, 2004.
Huddleston et al., "Clinical applications of microarray technology: creatine kinase B is an up-regulated gene epithelial ovarian cancer and shows promise as a serum marker," Gynecologic Oncology, vol. 96, pp. 77-83. (2005).
Ka S-M, et al., Urine Annexin A1 as an Index for Glomerular Injury in Patients. Dis. Markers.
Kroese et al., "Genetic tests and their evaluation: Can we answer the key questions?" Genetics in Medicine, vol. 5, No. 6, pp. 475-480, 2004.
Lemley, An introduction to biomarkers: applications to chronic kidney disease, Pediatric Nephrology, vol. 22, pp. 1849-1859, Mar. 2007.
Liu et al., "Increased Exosomal MicroRNA-21 and MicroRNA-146a Levels in the Cerviocovaginal Lavage Specimens of Patients with Cervical Cancer," Int. J. Mol. Sci. 2014, 15, 758-773; doi:10.33390/ijms15010758.
Lo, et al., "Defining the relationship between average glucose and HbA1c in patients with type 2 diabetes and chronic kidney diabetes," Diabetes Research and Clinical Practice, vol. 104, pp. 84-91, 2014, on line Feb. 3, 2014.
Melé M, et al., The human transcriptome across tissues and individuals. Science 348: 660-665, 2015.
Mi H, et al., Large-scale gene function analysis with the PANTHER classification system. Nat. Protoc. 8: 1551-1566, 2013.
Mikkola and Orkin, "The journey of developing hematopoietic stem cells,"Development 133, 3733-3744 (2006).
Obeidat, et al., "Post-transplant nuclear renal scans correlate with renal injury biomarkers and early allograft outcomes," Nephrol Dial Transplant (2011) 26: 3038-3045.
Ogura, et al., "Potential amelioration of upregulated renal HIF-1alpha-endothelin-1 system by landiolol hydrochloride in a rat model of endotoxemia," Life Sciences 1 18 (2014) 347-356.
OPTN: Organ Procurement and Transplantation Network—OPTN [Internet]. 2015 Available from: http://optn.transplant.hrsa.gov/ [cited Jun. 27, 2015].
Pepe, et al, "Phases of Biomarker Development for Early Detection of Cancer," Journal of the National Cancer Institute, vol. 93, No. 14, pp. 1054-1061, Jul. 2001.
Perez A, et al., A Pilot Study on the Potential of RNA-Associated to Urinary Vesicles as a Suitable Non-Invasive Source for Diagnostic Purposes in Bladder Cancer. Cancers 6: 179-192, 2014.
Properzi F, et al., Exosomes: the future of biomarkers in medicine. Biomark. Med. 7: 769-778, 2013.
R Core Team: R: The R Project for Statistical Computing [Internet]. R Lang. Environ. Stat. Comput. R Found. Stat. Comput. Vienna Austria. Available from: http://www.r-project.org/ [cited Jun. 15, 2015].
Reeve J, et al., Molecular Diagnosis of T Cell-Mediated Rejection in Human Kidney Transplant Biopsies. Am. J. Transplant. 13: 645-655, 2012.
Roedder S, et al., The kSORT Assay to Detect Renal Transplant Patients at High Risk for Acute Rejection: Results of the Multicenter AART Study. PLoS Med 11: e1001759, 2014.
Savage, et al., "New Prognostic Markers: The Pathway from Research to Clinical Practice," Grand rounds Urol. Aug. 8, 2009 (3): 7-13.
Sellarés J, et al., Molecular Diagnosis of Antibody-Mediated Rejection in Human Kidney Transplants. Am. J. Transplant. 13: 971-983, 2012.
Shipman, et al., "Effect of chronic kidney disease on A1C in individuals being screened for diabetes," Primary Care Diabetes 9 (2014) 142-146.
Sing T, et al., ROCR: visualizing classifier performance in R. Bioinformatics 21: 3940-3941, 2005.
Smith ZL, et al., Urinary markers for bladder cancer. F1000Prime Rep. [Internet] 5: 2013 Available from: http://www.ncbi.nlm.nih.gov/pmc/articles/PMC3702217/ [cited Aug. 17, 2015].
Spasovski et al., Proteomics in chronic kidney disease: The issues clinical nephrologists need an answer for, Clinical Applications, vol. 5, Nos. 5-6, pp. 233-240, Apr. 28, 2011.
Suthanthiran M, et al., Urinary-Cell mRNA Profile and Acute Cellular Rejection in Kidney Allografts. N. Engl. J. Med. 369: 20-31, 2013.
Tankova, et al., "Assessment of HbA1c as a diagnostic tool in diabetes and prediabetes," Acta Diabetol (2012) 49:371-378.
Taub et al., Role of biomarkers in the diagnosis and prognosis of acute kidney injury in patients with cardiorenal syndrome, Expert Review of Cardiovascular Therapy, vol. 10, No. 5, pp. 657-667, May 1, 2012.
The Cancer Genome Atlas Research Network: Comprehensive molecular characterization of urothelial bladder carcinoma. Nature

(56) References Cited

OTHER PUBLICATIONS

[Internet] advance online publication: 2014 Available from: http://www.nature.com/nature/journal/vaop/ncurrent/full/nature12965.html [cited Feb. 21, 2014].
Théry C, et al., Exosomes: composition, biogenesis and function. Nat. Rev. Immunol. 2: 569-579, 2002.
Théry C, et al., Membrane vesicles as conveyors of immune responses. Nat. Rev. Immunol. 9: 581-593, 2009.
Vaidya, et al., Biomarkers of acute kidney injury, Annual Review of Pharmacology and Toxicology, Annual Review Inc., vol. 48, pp. 463-493, Feb. 1, 2008.
Waikar et al., Diagnosis, Epidemiology and Outcomes of Acute Kidney Injury, Clinical Journal of the American Society of Nephrology, vol. 3, No. 3, pp. 844-861, Feb. 20, 2008.
Yuan Y, et al. Urinary candidate biomarker discovery in a rat unilateral ureteral obstruction model. Sci. Rep., Mar. 20, 2015.
Zhou et al., "Acute Kidney Injury Biomarkers—Needs, Present Status, and Future Promise," Nephrol Self Assess Program. Mar. 2006; 5(2):63-71.
Zhou et al., Exosomal Fetuin-A identified by proteomics: A novel urinary biomarker for detecting acute kidney injury, Kidney International, Nature Publishing Group, vol. 70, No. 10, Nov. 1, 2006, pp. 1847-1857.
Akoglu et al.: "Interleukin-2 in CD8+ T cells correlates with Banff score during organ rejection in liver transplant recipients," Clin Exp Med (2009) 9:259-262.
Bangs Laboratories Tech Note 204, Adsorption to Microspheres, Apr. 9, 2008 (printed from Internet Jan. 18, 2012 from <http://www.bangslabs.com/sites/default/files/bangs/docs.pdf/204.pdf>).
Grams et al.: "Fluid Balance, Diuretic Use, and Mortality in Acute Kidney Injury," Clin J Am Soc Nephrol 6:966-973, Mar. 10, 2011.
Harada, et al., "Non-Invasive Diagnosis of Post Kidney Transplant Complications," Urinary ExomL mRNA Analysis, May 4, 2015, Abstract No. 182.
Heemskerk, et al., "Upregulation of Renal Inducible Nitric Oxide Synthase during Human Endotoxemia and Sepsis Is Associated with Proximal Tubule Injury," Clin J. Am Soc Nephrol 1:853-862, 2006.
Kim et al.: "Predictive value of progression-related gene classifier in primay non-muscle invasive bladder cancer," Molecular Cancer 2010, 9:3 (2010).
Lebedev et al., Oligonucleotides containing 2-aminoadenine and 5-methylcyotsine are more effective as primers for PCR amplification than their normal nonmodified counterparts, Gen Anal (1996) vol. 13(1):15-21.
Masyuk, et al.: "Exosomes in the pathogenesis, diagnostics and therapeutics of liver diseases," Journal of Hepatology 2013 vol. 59, 621-625.
Millán, et al.: "Intracellular IFN-Y and IL-2 expression monitoring as surrogate markers of the risk of acute rejection and personal drug response in de novo liver transplant recipients," Cytokine 61 (2013) 556-564.
Mitsuhashi et al., Quantification of mRNA in Whole Blood by Assessing Recovery of RNA and Efficiency of cDNA Synthesis, Clin Chem (2006) vol. 52(4):634-642.
Mitsuhashi, Ex vivo simulation of leukocyte function: Stimulation of specific subset of leukocytes in whole blood followed by the measurement of function-associated nRNAs, J Immun Meth (2010) vol. 363(1):95-100.
Peake et al., "A comparison of the ability of levels of urinary biomarker proteins and exosomal mRNA to predict outcomes after renal transplantation," PLoS One, Jun. 11, 2014, vol. 9, No. 2, e98644, pp. 1-7.
Pisitkun et al., "Application of systems biology principles to protein biomarker discovery: urinary exosomal proteome in renal transplantation," Proteomics Clin Appl, Jun. 29, 2012, vol. 6, No. 5-6, pp. 268-278.
Rahman et al.: "Acute Kidney Injury: A Guide to Diagnosis and Management," Family Physican 86 (7) 2012, 631-639 (2012).
Umeshita et al.: "Determination of the Presence of Interleukin-6 in Bile After Orthotopic Liver Transplantation," Annals of Surgery, vol. 223, No. 2, 204-211. 1996.
Vollenhofer-Schrumpf et al., A simple nucleic acid hybridization/latex agglutination assay for the rapid detection of polymerase chain reaction amplicons, J Microbiol Methods (2007) vol. 68(3):568-576.
Wakabayashi, Therapeutic Research, 2001, vol. 22, No. 11, p. 2433-2437.
Warlé et al.: "Early Differentiation Between Rejection and Infection in Liver Transplant Patients by Serum and Biliary Cytokine Patterns," Transplantation, vol. 75, 146-151, No. 1, Jan. 15, 2003.
Wu et al., Detection of PCR amplicons from bacterial pathogens using microsphere agglutination, J Microbiol Meth (2004) vol. 56:395-400.

* cited by examiner

| | | | | | | | | | | |
|---|---|---|---|---|---|---|---|---|---|---|
| PDCN | This method | 30.3 | 32.0 | 33.3 | 31.9 | 33.4 | 30.6 | 32.4 | 31.6 | 31.9 | 1.1 | 3.5% |
| | Ultracentrifuge | 33.9 | 31.2 | 40.0 | 31.8 | 32.5 | 40.0 | 33.2 | 40.0 | 35.3 | 4.0 | 11.2% |
| SLC12A1 | This method | 27.1 | 27.7 | 26.4 | 26.9 | 27.1 | 26.8 | 27.6 | 26.9 | 27.1 | 0.4 | 1.5% |
| | Ultracentrifuge | 29.8 | 26.5 | 28.6 | 26.4 | 27.5 | 29.2 | 27.5 | 29.6 | 28.1 | 1.4 | 4.8% |
| ALB | This method | 25.9 | 26.2 | 24.9 | 25.5 | 25.9 | 25.7 | 26.2 | 25.5 | 25.7 | 0.4 | 1.7% |
| | Ultracentrifuge | 28.9 | 25.9 | 30.6 | 25.4 | 27.1 | 28.5 | 27.2 | 28.3 | 27.7 | 1.7 | 6.1% |
| Uromodulin | This method | 29.3 | 29.5 | 28.8 | 29.5 | 28.6 | 28.7 | 29.6 | 29.6 | 29.2 | 0.4 | 1.4% |
| | Ultracentrifuge | 30.8 | 28.4 | 33.1 | 29.1 | 30.2 | 30.6 | 30.9 | 31.6 | 30.6 | 1.5 | 4.8% |
| AQP2 | This method | 30.4 | 31.7 | 29.8 | 29.3 | 31.5 | 29.7 | 29.1 | 29.9 | 30.2 | 1.0 | 3.2% |
| | Ultracentrifuge | 40.0 | 30.1 | 32.5 | 29.0 | 30.6 | 40.0 | 29.9 | 40.0 | 34.0 | 5.1 | 14.9% |

FIG. 8-2

DEVICES AND METHODS FOR CAPTURING TARGET MOLECULES

RELATED CASES

The entire disclosure of each of the applications listed in the accompanying Application Data Sheet is incorporated by reference herein.

BACKGROUND

Field

The present disclosure relates to systems, devices and methods for the enhanced efficiency of capturing agents of interest from fluid samples. The fluid samples are biological fluid samples in some embodiments, while in other embodiments, non-biological fluid samples are used. For example, in several embodiments, environmental water samples are passed through the devices as disclosed herein in order to assess, for example, mineral content, pollution levels, chemical or toxin content, presence of pathogens, etc.

Description of Related Art

Often it is desirable to extract certain components from a liquid. For example, many medical tests analyze biomarkers in a fluid sample (e.g., blood, urine, etc.) taken from a patient. Diagnosis or prognosis may be derived from identification of a biomarker or a biochemical pattern that is not present in healthy patients or is altered from a previously obtained patient sample.

Frequently, the use of bodily fluids to isolate or detect a biomarker significantly dilutes the biomarker. Moreover, most biomarkers are produced in low or even moderate amounts in tissues and bodily fluids. Diagnosis or prognosis is likely less accurate when the compounds of interest are present at low concentrations.

SUMMARY

In several embodiments, there are provided systems and methods for the efficient collection of biomarkers from fluid samples, such as biological fluid samples. For example, in several embodiments, there is provided a system for capturing vesicles from a biological fluid sample obtained from a subject, comprising (i) a vesicle capture device, comprising (a) a first body having an inlet, an outlet, and an interior volume between the inlet and the outlet, (b) a second body having an inlet, an outlet, an interior volume between the inlet and the outlet, a filter material positioned within the interior volume of the second body, and in fluid communication with said first body, wherein the first body and the second body are reversibly connected by an interaction of the inlet of the second body with the outlet of the first body, (ii) a receiving vessel having an interior cavity, and wherein the interior cavity of the receiving vessel is dimensioned to reversibly enclose both the first and the second body and to receive the biological fluid sample after it is passed from the interior volume of the first body, through the filter material, through the interior cavity of the second body and out of the outlet of the second body.

In several embodiments, the system further comprises (iii) one or more analysis wells configured to reversibly interact with the outlet of an individual second body. In some embodiments, the analysis wells comprise a single tube, such as, for example, a microcentrifuge tube. In several embodiments, however, the one or more analysis wells comprise a standard 6-, 12-, 48-, or 96-well microplate. In one embodiment, the one or more analysis wells comprises a standard 96-well microplate.

Additionally, in several embodiments, there is provided a system for capturing vesicles from a biological fluid sample obtained from a subject, comprising (i) a vesicle capture device, comprising (a) a first body having an inlet, an outlet, and an interior volume between the inlet and the outlet, (b) a second body having an inlet, an outlet, an interior volume between the inlet and the outlet, a filter material positioned within the interior volume of the second body, and in fluid communication with said first body, wherein the first body and the second body are reversibly connected by an interaction of the inlet of the second body with the outlet of the first body, wherein said interaction comprises insertion of the outlet of the first body into the inlet of the second body, wherein the second body is disconnected from the first body by extracting the outlet of the first body from the inlet of the second body, wherein the outlet of the second body is dimensioned to fit within the inner diameter of a well of a 6, 12, 48, or 96-well microplate, wherein the second body comprises a unique identifier that corresponds to the identity of said subject; and (ii) a receiving vessel having an inlet, a closed end opposite the inlet and interior cavity, wherein the interior cavity of the receiving vessel is dimensioned to reversibly enclose both the first and the second body and to receive the biological fluid sample after it is passed from the interior volume of the first body, through the filter material, through the interior cavity of the second body and out of the outlet of the second body.

In several embodiments, the interior volume of the first body ranges from about 2 to about 10 mL. In several embodiments, the interior volume of the second body ranges from about 2 to about 5 mL.

In several embodiments, the reversible connection between the inlet of the second body with the outlet of the first body comprises a friction connection. In several embodiments, the reversible connection between the inlet of the second body with the outlet of the first body comprises a luer lock connection. In several embodiments, the reversible connection between the inlet of the second body with the outlet of the first body comprises rotational connection wherein a pin on the outlet of the second body mates with a groove on the inlet of the second body. In several embodiments, the reversible connection between the inlet of the second body with the outlet of the first body comprises a threaded connection. In some embodiments, the inlet of the second body comprises female threads on the inlet of the second body that mate with male threads on the outlet of the first body. In additional embodiments, the inlet of the second body comprises male threads on the inlet of the second body that mate with female threads on the outlet of the first body. In several embodiments, the connection is configured to allow the second body to be coupled and later de-coupled from the first body without the second body having to pass through the interior volume of the first body.

In several embodiments, the unique identifier on the second body comprises a patient specific RFID tag. In several embodiments, the unique identifier on the second body comprises a patient specific 2-dimensional bar code. In several embodiments, the unique identifier on the second body comprises a patient specific 3-dimensional bar code. In several embodiments, the unique identifier on the second body is visible and/or readable from a position above the second body, when the outlet of said second body is in communication with analysis wells. In several embodiments, other visual, electronic, or magnetic unique patient identifiers are used.

In several embodiments, the interior cavity of the receiving vessel has a volume of about 50 mL. In several embodiments, the interior cavity of the receiving vessel has a volume of about 100 mL.

In several embodiments, the first body comprises a lip extending from a perimeter of the inlet of the first body, and wherein said lip rests on a perimeter of the inlet of the receiving vessel and allows the receiving vessel to enclose the first and second bodies while allowing removal of the first and second bodies from the receiving vessel. In several embodiments, the lip on the first body holds the first and second body in a fixed position within the interior cavity of the receiving vessel. Advantageously, in several embodiments, the fixed position is a position in which the outlet of the second body does not contact the biological fluid sample that has passed from the interior volume of the first body, through the filter material and into the interior cavity of the receiving vessel.

In several embodiments, the receiving vessel consists essentially of the inlet, the closed end opposite the inlet and the interior cavity (e.g., the receiving vessel has no additional ports or openings).

In several embodiments, centrifugation is used to pass said biological fluid sample from the interior of the first body, through the filter material, out the outlet of the second body and into the interior volume of the receiving vessel.

In several embodiments, the filter material comprises a plurality of layers of one or more glass-like materials configured to retain vesicles having a diameter of from about 0.6 microns to about 1.5 microns in diameter.

In several embodiments, the system does not employ negative or positive pressure to pass said biological fluid sample from the interior of the first body, through the filter material, out the outlet of the second body and into the interior volume of the receiving vessel.

There are additionally provided methods for isolating vesicles from a biological fluid sample, the methods comprising, obtaining a system comprising a first body having an inlet, an outlet, and an interior volume between the inlet and the outlet, a second body having an inlet, an outlet, an interior volume between the inlet and the outlet, a filter material positioned within the interior volume of the second body, and in fluid communication with said first body, wherein the first body and the second body are reversibly connected by an interaction of the inlet of the second body with the outlet of the first body, a receiving vessel having an interior cavity, and wherein the interior cavity of the receiving vessel is dimensioned to reversibly enclose both the first and the second body and to receive the biological fluid sample after it is passed from the interior volume of the first body, through the filter material, through the interior cavity of the second body and out of the outlet of the second body, placing a volume of a biological fluid sample into interior volume of the first body via the inlet of the first body, wherein the first body is reversibly connected to the second body, placing the first and second bodies into the interior cavity of the receiving vessel, applying one or more of gravitational or centrifugal force to the receiving vessel, thereby causing the biological sample to pass from the interior volume of the first body, through the filter material of the second body, out the outlet of the second body and into the interior cavity of the receiving vessel, wherein the filter captures vesicles from the biological fluid sample, thereby isolating a vesicle from said biological fluid sample.

In several embodiments, the method further comprises detecting expression of a gene of interest from biological fluid sample, extracting the first and second bodies from the receiving vessel; disconnecting the first and second body from one another; placing the outlet of the second body in communication with a well of a 96-well microplate; introducing an elution buffer into the inlet of the second body, wherein said elution buffer comprises a buffer that lyses said vesicles captured on the filter of the second body, thereby releasing RNA from said vesicle; transferring said released RNA from said filter to the corresponding well of the 96-well microplate; and detecting expression of said gene of interest by a method comprising: (i) contacting said RNA with a reverse transcriptase to generate complementary DNA (cDNA), and (ii) contacting said cDNA with sense and antisense primers that are specific for said gene of interest and a DNA polymerase to generate amplified DNA, thereby detecting expression of said gene of interest. In additional embodiments, other microplate sizes (or individual tubes or arrays of tubes) may also be used.

Additionally provided is a system for capturing vesicles from a biological fluid sample obtained from a subject, comprising (i) a vesicle capture device, comprising: (a) a first body having an inlet, an outlet, and an interior volume between the inlet and the outlet; (b) a second body having an inlet, an outlet, an interior volume between the inlet and the outlet, a filter material positioned within the interior volume of the second body, having a unique identifier comprising a patient specific RFID tag, and in fluid communication with said first body, wherein the first body and the second body are reversibly connected by an interaction of the inlet of the second body with the outlet of the first body; (ii) a receiving vessel having an interior cavity, and wherein the interior cavity of the receiving vessel is dimensioned to reversibly enclose both the first and the second body and to receive the biological fluid sample after it is passed from the interior volume of the first body, through the filter material, through the interior cavity of the second body and out of the outlet of the second body.

Additionally provided is a system for capturing vesicles from a biological fluid sample obtained from a subject, comprising: (i) a vesicle capture device, comprising: (a) a first body having an inlet, an outlet, and an interior volume between the inlet and the outlet; (b) a second body having an inlet, an outlet, an interior volume between the inlet and the outlet, a filter material positioned within the interior volume of the second body, having a unique identifier comprising a patient specific 2-dimensional bar code, and in fluid communication with said first body, wherein the first body and the second body are reversibly connected by an interaction of the inlet of the second body with the outlet of the first body; (ii) a receiving vessel having an interior cavity, and wherein the interior cavity of the receiving vessel is dimensioned to reversibly enclose both the first and the second body and to receive the biological fluid sample after it is passed from the interior volume of the first body, through the filter material, through the interior cavity of the second body and out of the outlet of the second body.

Additionally provided is a system for capturing vesicles from a biological fluid sample obtained from a subject, comprising: (i) a vesicle capture device, comprising: (a) a first body having an inlet, an outlet, and an interior volume between the inlet and the outlet; (b) a second body having an inlet, an outlet, an interior volume between the inlet and the outlet, a filter material positioned within the interior volume of the second body, having a unique identifier comprising a patient specific 3-dimensional bar code, and in fluid communication with said first body, wherein the first body and the second body are reversibly connected by an interaction of the inlet of the second body with the outlet of the first body; (ii) a receiving vessel having an interior cavity, and wherein the interior cavity of the receiving vessel is dimensioned to reversibly enclose both the first and the second body and to receive the biological fluid sample after it is passed from the interior volume of the first body, through the filter material, through the interior cavity of the second body and out of the outlet of the second body.

Additionally provided is a system for capturing vesicles from a biological fluid sample obtained from a subject, comprising: (i) a vesicle capture device, comprising: (a) a first body having an inlet, an outlet, and an interior volume between the inlet and the outlet; (b) a second body having an inlet, an outlet, an interior volume between the inlet and the outlet, a filter material positioned within the interior volume of the second body, and in fluid communication with said first body, wherein the first body and the second body are reversibly connected by an interaction of the inlet of the second body with the outlet of the first body, wherein said interaction comprises an interaction between female threads on the inlet of the second body that mate with male threads on the outlet of the first body; (ii) a receiving vessel having an interior cavity, and wherein the interior cavity of the receiving vessel is dimensioned to reversibly enclose both the first and the second body and to receive the biological fluid sample after it is passed from the interior volume of the first body, through the filter material, through the interior cavity of the second body and out of the outlet of the second body.

Additionally provided is a system for capturing vesicles from a biological fluid sample obtained from a subject, comprising: (i) a vesicle capture device, comprising: (a) a first body having an inlet, an outlet, and an interior volume between the inlet and the outlet; (b) a second body having an inlet, an outlet, an interior volume between the inlet and the outlet, a filter material positioned within the interior volume of the second body, and in fluid communication with said first body, wherein the first body and the second body are reversibly connected by an interaction of the inlet of the second body with the outlet of the first body, wherein said interaction comprises an interaction between male threads on the inlet of the second body that mate with female threads on the outlet of the first body; (ii) a receiving vessel having an interior cavity, and wherein the interior cavity of the receiving vessel is dimensioned to reversibly enclose both the first and the second body and to receive the biological fluid sample after it is passed from the interior volume of the first body, through the filter material, through the interior cavity of the second body and out of the outlet of the second body.

In several embodiments, the reversible connections between the first and second body is configured to allow disconnection of the second body from the first body without the second body passing through the interior volume of the first body.

In several embodiments, these systems further comprise (iii) one or more analysis wells configured to reversibly interact with the outlet of an individual second body.

In several embodiments wherein a microplate is used, a frame is positioned between the vesicle capture device second body in order to improve the stability of the interaction between the second hollow body and the microplate. In several embodiments, after placing the second hollow body into the microplate (e.g., through the frame) a lysis buffer is added and incubated at 37° C. for 1-20 (e.g., 10) minutes to release mRNA from captured exosomes. In several embodiments, the frame was then placed onto oligo (dT)-immobilized plate and centrifuged for 1-10 (e.g., 5) minutes at ~2000×g at ~4° C. The resultant oligo(dT)-immobilized plate was stored at ~4° C. overnight (e.g., 14 to 24 hours) for the hybridization between poly(A)+ tail of mRNA and immobilized oligo(dT) as described previously. In several embodiments, non-mRNA materials are removed by washing and cDNA is generated, which can used for real time PCR (or other analysis methods). This process can also be used when a non-microplate format (e.g., tube or array of tubes) is used, as well as when no microplate frame is used. Moreover, additional embodiments, employ different reaction conditions and/or times.

Given that accurate diagnosis may be hampered (or even impossible) when a target compound of interest is present in a biological sample at low concentrations, there is a need for devices and methods for extracting biomarkers and other components of interest from a fluid sample of a patient without unduly lowering the concentration of the target biomarker. Extraction of fluid components is beneficial in many contexts including, but not limited to, filtration, purification, isolation, and enrichment.

Thus, several embodiments of the devices and methods allow extraction of target components from liquids. In particular, the devices and methods disclosed herein are useful for capturing from biological fluids nucleic acids, exosomes, vesicles, and other circulating membrane bound nucleic acid and/or protein-containing structures. However, as the devices and methods disclosed herein permit extraction of organic and non-organic compounds, the devices and methods disclosed herein are applicable to fluid samples of biological or non-biological origin.

Conventional methods of vesicle and exosome extraction often involve ultracentrifugation in order to separate the vesicles from other matter in a biological sample. Ultracentrifugation is accomplished through the use of expensive and potentially hazardous equipment. Moreover, ultracentrifugation often results in samples being collected in multiple tubes. Consequently, ultracentrifugation is sometimes an impractical or impossible technique for many laboratories.

Therefore, provided herein are devices and methods for capture of nucleic acids, exosomes, vesicles, and other circulating membrane-bound nucleic acid and/or protein-containing structures that are released from cells into biological fluids. In several embodiments the devices and methods as disclosed herein provide several advantages over traditional techniques for vesicle isolation, such as ultracentrifugation. For example, in some embodiments the devices and methods disclosed herein capture vesicles, exosomes, and/or biomarkers from samples and advantageously allow multiple filtrations of samples through the same filter. Consequently, increased amounts of vesicle material can be collected simply by applying multiple sample aliquots to a device. In some embodiments, vesicle yield is increased by re-passing the filtrate of a sample aliquot through the device.

In several embodiments, there is provided a method of isolating vesicles from biological fluid, comprising: (a) obtaining a biological fluid sample comprising said vesicles; (b) adjusting the salt concentration of the fluid sample to between about 10 mM and 800 mM; (c) adjusting the pH of the fluid sample to between about pH 6 and pH 9; and (d) passing said biological fluid sample through a vesicle-capture material, said vesicle-capture material comprising glass-like materials, wherein the vesicles from said biological fluid sample are captured on or in said vesicle-capture material.

In several embodiments, a sample aliquot is subjected to centrifugation before passing the sample aliquot through the vesicle-capture material. In some embodiments, the supernatant generated by said centrifugation is discarded, while in other embodiments it is passed through said capture materials one or more additional times to increase the yield of vesicles. In several embodiments, the fluid sample is urine. In several embodiments, the salt concentration is adjusted to between about 20 mM and 600 mM. In several embodiments, the salt concentration is based on the concentration of monovalent cations in the sample.

In several embodiments, the vesicle-capture material is pre-treated to remove a material that inhibits capture of the vesicles. In several embodiments, albumin is removed by pretreatment. In several embodiments, the material is pretreated by a method selected from the group consisting of heating, acid bath, basic bath, and ultrasonic cleaning.

In several embodiments, the adjusting comprises titrating said fluid sample with a concentrated salt and buffer solution to reach said salt concentration of between about 10 mM and 800 mM and said pH of between about pH 6 and about pH 9.

In several embodiments, the vesicle-capture material comprises glass-like materials. In several embodiments the vesicle-capture material comprises a plurality of layers of the material. In some embodiments, the retention rate of the vesicle-capture material is greater than 50%, 75%, 90% or 99% for vesicles having a diameter of from about 0.6 microns to about 1.5 microns in diameter. In one embodiment, the vesicle-capture material captures vesicles sized from about 0.7 microns to about 1.6 microns in diameter. In one embodiment, the vesicle-capture material captures exosomes or other vesicles ranging in size from about 0.020 to about 1.0 microns.

In several embodiments, the vesicle-capture material comprises a plurality of layers of material. In several embodiments, combinations of vesicle capture materials are used. In some embodiments, a plurality of glass-like materials is used. In several embodiments, the plurality of layers of the vesicle-capture material comprises at least a first layer and a second layer of glass fiber. In some embodiments, the biological fluid is passed through a first layer of glass fiber to capture material from the biological sample that is about 1.6 microns or greater in diameter. In some embodiments, the biological fluid is passed through a second layer of glass fiber to capture vesicles having a minimum size from about 0.6 microns to about 0.8 microns in diameter, and having a maximum size of less than 1.6 microns. In several embodiments, combinations of glass-like and non-glass-like materials are used. In one embodiment, a non-glass-like material comprising nitrocellulose is used in combination with a glass-like material.

In several embodiments, the vesicle-capture material is modified in order to tailor the profile of vesicles that are captured. In one embodiment, the zeta potential of the material is used as a basis for modification (e.g., electrostatic charging) of the material. In several embodiments, the material (based on its zeta potential) does not require modification.

In several embodiments, the methods disclosed herein further comprise eluting the vesicles from the vesicle-capture material. In some embodiments, the vesicle-capture material is optimized to balance the attractive nature of the vesicle-capture material and the ability of the vesicle-capture material to release captured vesicles. In some embodiments, vesicles are eluted from the vesicle-capture material by passing a chaotropic reagent through vesicle-capture material. In some embodiments, vesicles are eluted from the vesicle-capture material by passing a lysis buffer through vesicle-capture material.

In several embodiments, the vesicle-capture device is connected to a vacuum source in order to pass the biological fluid from the sample loading region through the vesicle-capture material and into the sample receiving region. In one embodiment, the passings are accomplished through the application of vacuum pressure to the device. In several embodiments, the vesicle-capture device can receive positive pressure in order to pass the biological fluid from the sample loading region through the vesicle-capture material and into the sample receiving region. In one embodiment, the passings are accomplished through the application of positive pressure to the device. In several embodiments, the device can be placed in a centrifuge in order to pass the biological fluid from the sample loading region through the vesicle-capture material and into the sample receiving region. In one embodiment, the passings are accomplished through low-speed centrifugation of the device. In some embodiments, the passage of the biological fluid into the sample receiving region is achieved by wicking-type materials. In several embodiments, the vesicle capture device is configured in a multi-well plate format.

There is also provided herein a method for isolating a biomarker, comprising isolating vesicles comprising at least one biomarker from a biological fluid by passing the biological fluid through a vesicle-capture material, removing non-vesicle material from the vesicle-capture material and lysing the vesicles in or on the vesicle-capture material with a lysis buffer, thereby isolating a biomarker from the vesicles.

In some embodiments, the biomarker is selected from the group consisting of RNA, DNA, protein, exosomes, vesicles, other circulating membrane bound nucleic acid and/or protein-containing structures and carbohydrate. In several embodiments, the RNA is of a type selected from the group consisting of mRNA, miRNA, rRNA, tRNA, and vRNA.

Some embodiments provide a device for the collection of vesicles from a biological fluid, the device comprising (1) at least one sample loading region; (2) at least one corresponding vesicle-capture material and (3) at least one corresponding sample receiving region, wherein passage of the biological fluid from the sample loading region through the vesicle-capture material and into the sample receiving region results in capture of vesicles within the biological fluid on or in the vesicle-capture material. In some embodiments, wherein the vesicle-capture material comprises glass-like materials, which have a structure that is disordered or "amorphous" at the atomic scale, like plastic or glass. Glass-like materials include, but are not limited to glass beads or fibers, silica beads (or other configuration), nitrocellulose, nylon, polyvinylidene fluoride (PVDF) or other similar polymers, metal or nano-metal fibers, polystyrene, ethylene vinyl acetate or other co-polymers, natural fibers (e.g., silk), alginate fiber, or combinations thereof. In certain embodiments, the vesicle-capture material optionally comprises a plurality of layers of vesicle-capture material. In other embodiments, the vesicle-capture material further comprises nitrocellulose. In some embodiments, the vesicle-capture material captures exosomes ranging in size from about 50 to about 100 nanometers.

Some embodiments provide a method of isolating vesicles from biological fluid, comprising (1) obtaining a biological sample comprising vesicles; (2) loading at least a portion of the biological sample into a sample loading region of a vesicle capture device; (3) passing the biological sample from the sample loading region through a vesicle-capture material in the vesicle capture device; and (4) passing the biological sample from the vesicle-capture material to a sample receiving region, wherein the passages of the biological sample results in capture of the vesicles within the biological fluid on or in the vesicle-capture material. In some embodiments, the method further comprises eluting the vesicles from the vesicle-capture material. In some embodiments, the method further comprises capturing, enriching, and/or condensing vesicles comprising RNA; removing non-vesicle material from the device; and lysing the vesicles in or on the vesicle-capture material with a lysis buffer, thereby isolating vesicle-associated RNA from the vesicles.

The methods summarized above and set forth in further detail below describe certain actions taken by a practitioner; however, it should be understood that they can also include the instruction of those actions by another party. Thus, actions such as "administering a blood test" include "instructing the administration of a blood test."

BRIEF DESCRIPTION OF THE FIGURES

FIGS. 8-1 and 8-2 depicts data related to the intra-assay variation when the devices disclosed herein are used to capture exosomes as compared to ultracentrifugation-based isolation.

DETAILED DESCRIPTION

General

Figure 1:
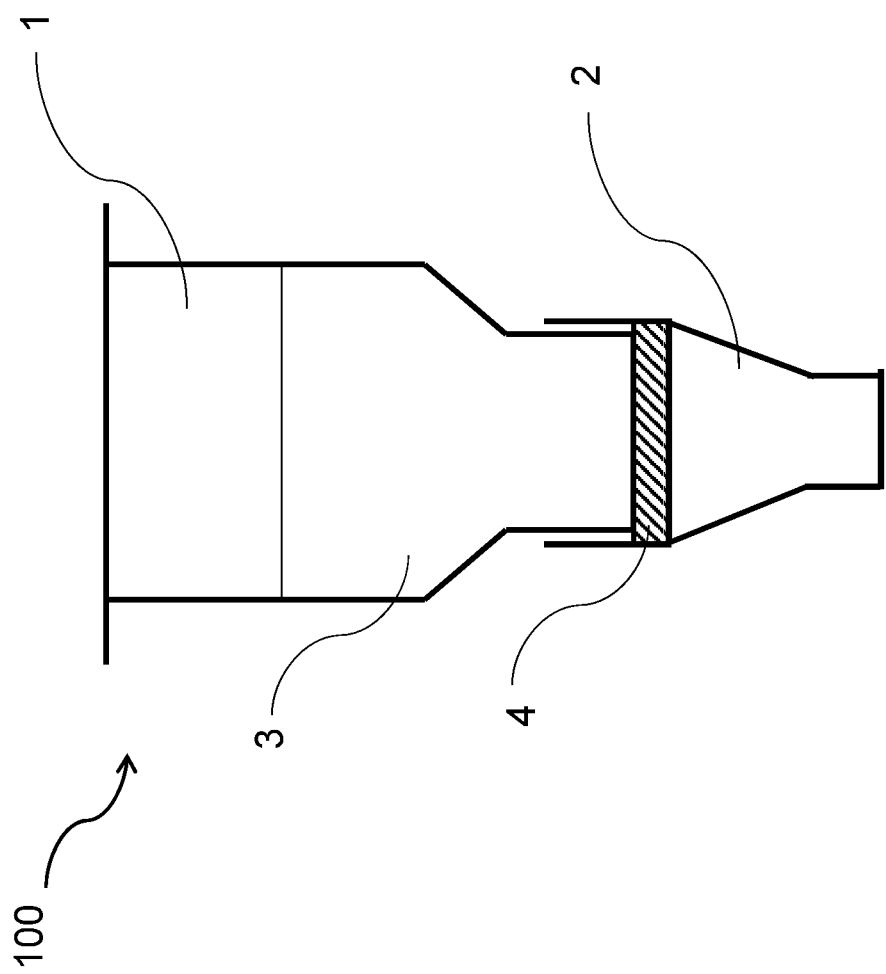
FIG. 1 is a cross-section view of one embodiment of a capture device as disclosed herein.

Due to the rapid rate of nucleic acid degradation in the extracellular environment, conventional understanding suggests that many tissues are unable to provide nucleic acid that would be suitable as a diagnostic target because the nucleic acids would be degraded before they could be used as a template for detection. However, extracellular RNA (as well as other biomarkers disclosed herein) is often associated with one or more different types of membrane particles (ranging in size from 50-80 nm), exosomes (ranging in size from 50-100 nm), exosome-like vesicles (ranging in size from 20-50 nm), and microvesicles (ranging in size from 100-1000 nm). Other vesicle types may also be captured, including, but not limited to, nanovesicles, vesicles, dexosomes, blebs, prostasomes, microparticles, intralumenal vesicles, endosomal-like vesicles or exocytosed vehicles. As used herein, the terms "exosomes" and "vesicles" are used in accordance with their respective ordinary meanings in this field and shall also be read to include any shed membrane bound particle that is derived from either the plasma membrane or an internal membrane. For clarity, the terms describing various types of vesicles shall, unless expressly stated otherwise, be generally referred to as vesicles or exosomes. Exosomes can also include cell-derived structures bounded by a lipid bilayer membrane arising from both herniated evagination (e.g., blebbing) separation and sealing of portions of the plasma membrane or from the export of any intracellular membrane-bounded vesicular structure containing various membrane-associated proteins of tumor origin, including surface-bound molecules derived from the host circulation that bind selectively to the tumor-derived proteins together with molecules contained in the exosome lumen, including but not limited to tumor-derived microRNAs or intracellular proteins. Exosomes can also include membrane fragments. Circulating tumor-derived exosomes (CTEs) as referenced herein are exosomes that are shed into circulation or bodily fluids from tumor cells. CTEs, as with cell-of-origin specific exosomes, typically have unique biomarkers that permit their isolation from bodily fluids in a highly specific manner. As achieved by several embodiments disclosed herein, selective isolation of any of such type of vesicles allows for isolation and analysis of their RNA (such as mRNA, microRNA, and siRNA) which can be useful in diagnosis or prognosis of numerous diseases. Thus, exosomes and microvesicles (EMV) can provide biomarkers for diseases (including, but not limited to, the isolation of vesicles from urine for the assessment of renal disease). Target compounds that can be extracted using the devices and methods herein disclosed include proteins, lipids, antibodies, vitamins, minerals, steroids, hormones, cholesterol, amino acids, vesicles, exosomes, and nucleic acids.

In several embodiments, biological fluid samples are processed. As used herein, a "bodily fluid" shall be given its ordinary meaning and shall also refer to a sample of fluid collected from the body of the subject, including but not limited to, for example, blood, plasma, serum, urine, sputum, spinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof.

In several embodiments, a biological fluid sample is processed by using a system configured to capture a target of interest from the fluid. Generally speaking several embodiments of the system comprise a first fluid compartment having a first volume, the first compartment being configured to reversibly interconnect to a second fluid compartment comprising an agent capture material, with both the first and second compartment being dimensioned to fit within an outer housing. In several embodiments, the outer housing functions to receive eluate (e.g., the biological sample depleted of the target of interest).

In several embodiments the system is particularly advantageous in that it allows a high degree of concentration of agents of interest that are present at low concentrations in a fluid sample.

One aspect of the present disclosure relates to devices and methods for the enhanced efficiency of capturing exosomes, vesicles, and other circulating membrane bound nucleic acid and/or protein-containing structures from biological fluids.

These devices and methods can advantageously be employed even when the individual samples have varied characteristics. The captured exosomes, vesicles and other circulating membrane bound nucleic acid and/or protein-containing structures may contain a variety of different specific biomarkers, which can be employed in a variety of diagnostic, prognostic and therapeutic and other medically-related methods and uses.

FIG. 1 depicts an embodiment of a capture device 100. The embodiment of capture device 100 depicted in FIG. 1 comprises a first hollow body 1 in functional communication with a second hollow body 2. "Functional communication" shall be given its ordinary meaning and shall also refer to the two hollow bodies being coupled in such a manner that it is possible to carry out an intended use of the device. Direct and indirect connections are within the scope of the meaning of "functional communication."

In several embodiments, a fluid sample 3 is loaded into first hollow body 1 and passed to second hollow body 2. In several embodiments, fluid sample 3 passes through a capture material 4. Fluid sample 3 may contain a target component. In some embodiments, as fluid sample 3 passes through capture material 4, capture material 4 retains at least some of the target component contained in fluid sample 3. In some embodiments, a target component comprises at least one exosome though other components whose isolation or purification is desirable may also be considered as target components.

In some embodiments, capture material 4 is located within second hollow body 2. In several embodiments, after fluid sample 3 has passed through capture material 4, second hollow body 2 is removed from first hollow body 1, and second hollow body 2 is then processed to retrieve the target components retained in capture material 4. In at least one embodiment, exosomes that have been retained by capture material 4 are subsequently recovered from capture material 4 by passing a small amount of liquid (e.g., a lysis buffer) through capture material 4. In some embodiments, another solution (e.g., a washing buffer) is optionally passed through capture material 4 before and/or after application of the liquid used to recover the retained exosomes.

In some embodiments, gravitational force drives the passage of fluid sample 3 through capture material 4. In some embodiments, a positive pressure drives fluid sample 3 through capture material 4. In some embodiments, a negative pressure drives fluid sample 3 through capture material 4. In several embodiments, no negative or positive pressure is used. In some embodiments, centrifugal force drives fluid sample 3 through capture material 4. In some embodiments, a wicking-type material drives fluid sample 3 through capture material 4. In some embodiments, capillary action drives fluid sample 3 through capture material 4.

Fluid sample 3 can be any liquid including bodily fluids. "Bodily fluid" shall be given its ordinary meaning and shall also refer to a sample of fluid isolated from anywhere in the body of the subject, including but not limited to, for example, blood, plasma, serum, urine, sputum, spinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid, and combinations thereof.

Figure 2:
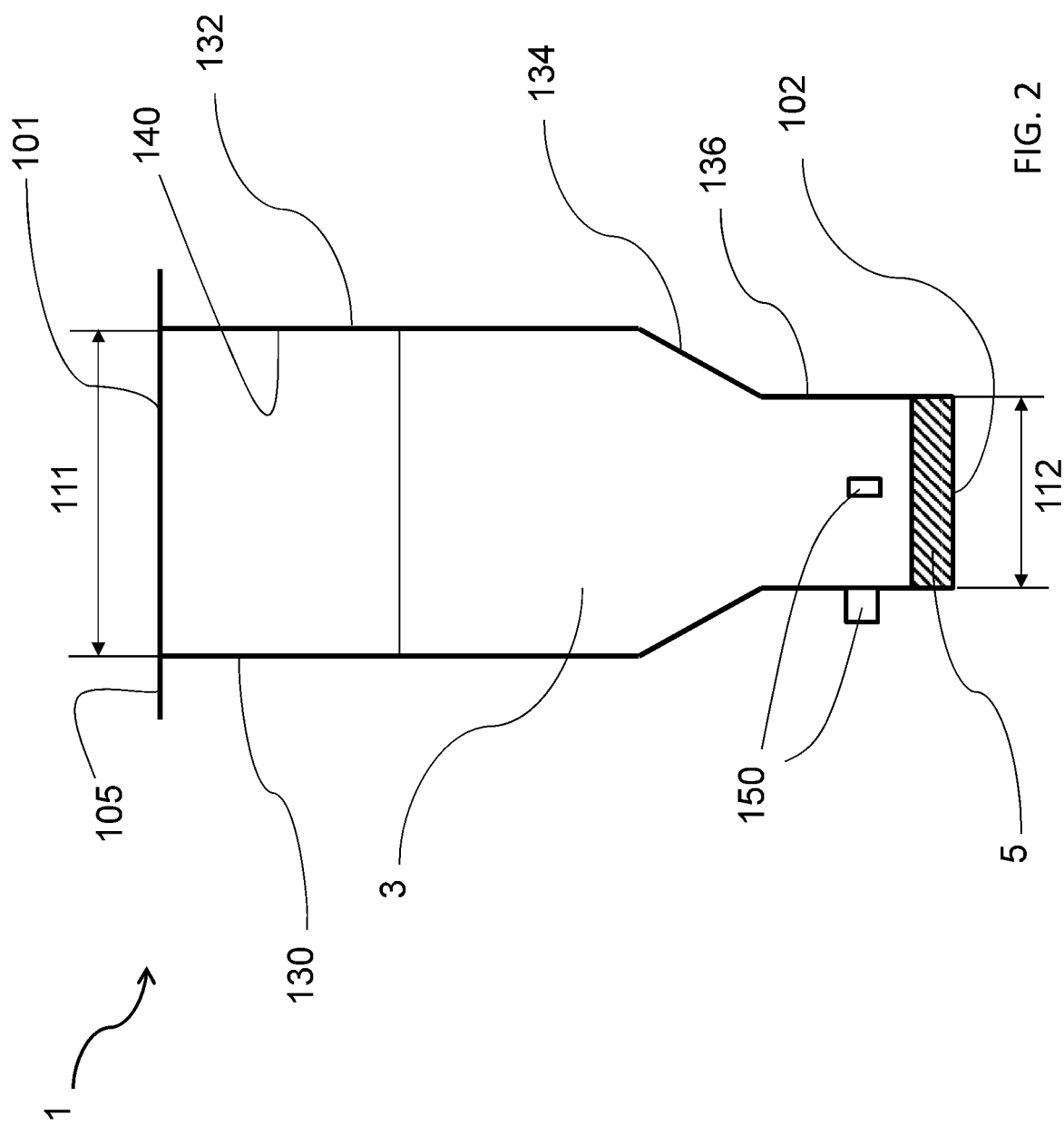
FIG. 2 is a cross-section view of one embodiment of a first hollow body as disclosed herein.

FIG. 2 depicts one embodiment of first hollow body 1. In several embodiments, first hollow body 1 has an inlet opening 101, an outlet opening 102, an outer surface 130, and an inner surface 140. In some embodiments, inlet opening 101 is a circular opening having an inlet diameter 111. In some embodiments, outlet opening 102 is a circular opening having an outlet diameter 112. In several embodiments, inlet opening 101 and outlet opening 102 are circular openings that are axially-aligned, with outlet diameter 112 being smaller than inlet diameter 111.

In some embodiments, first hollow body 1 comprises an upper region 132, an intermediate region 134, and a terminal region 136. In some embodiments, upper region 132 and terminal region 136 are cylindrical or substantially cylindrical, and intermediate region 134 is tapered (e.g., conical). In some embodiments, the taper of intermediate region 134 is configured to facilitate passage of fluid sample 3 through outlet opening 102. In some embodiments, first hollow body 1 includes a collar 105 that extends beyond outer surface 130 of an adjacent portion of first hollow body 1. In some embodiments, collar 105 is configured to support first hollow body 1 when first hollow body 1 is inserted into a storage rack or a receiving vessel (not shown).

Figure 3:
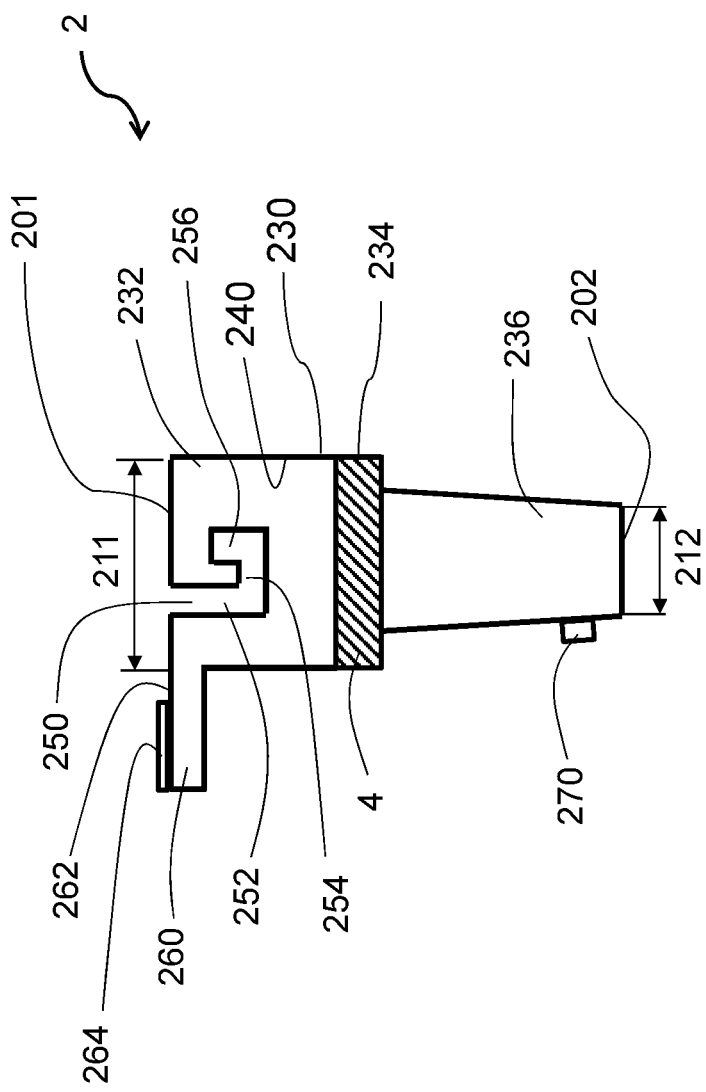
FIG. 3 is a cross-section view of one embodiment of a second hollow body as disclosed herein.
Figure 4:
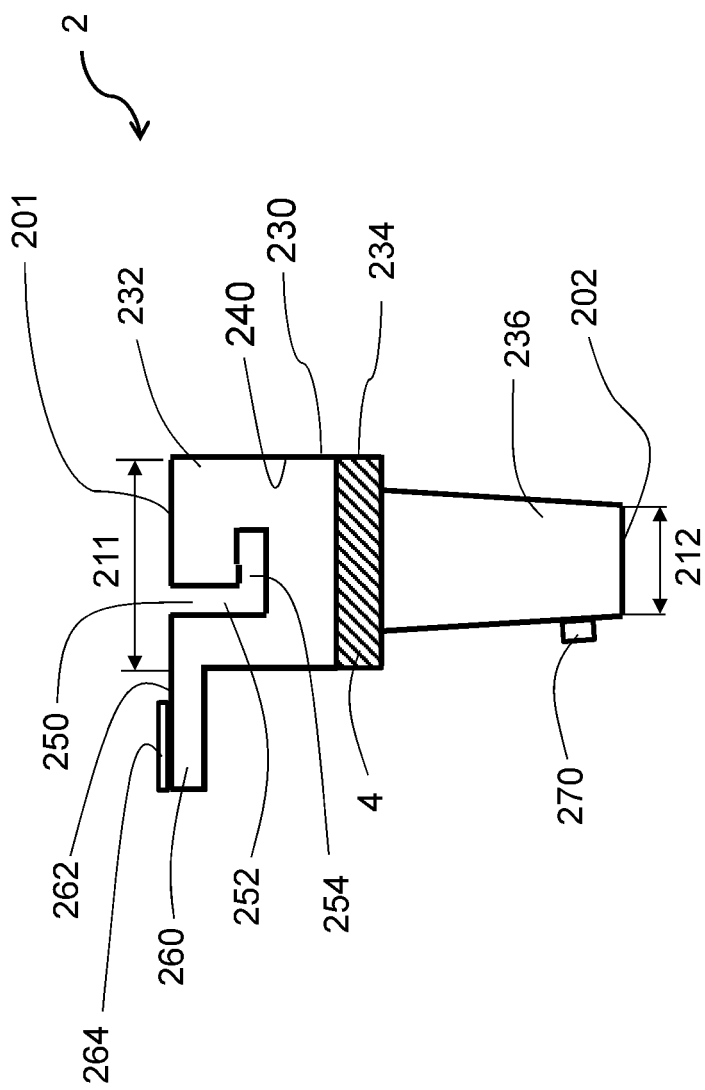
FIG. 4 is a cross-section view of an additional embodiment of a second hollow body as disclosed herein.

FIG. 3 depicts an embodiment of second hollow body 2. In several embodiments, second hollow body 2 has an inlet opening 201, an outlet opening 202, an outer surface 230, and an inner surface 240. In some embodiments, inlet opening 201 is a circular opening having an inlet diameter 211. In some embodiments, outlet opening 202 is a circular opening having an outlet diameter 212. In several embodiments, inlet opening 201 and outlet opening 202 are circular openings that are axially-aligned, with outlet diameter 212 being smaller than inlet diameter 211.

In several embodiments, first hollow body 1 and second hollow body 2 are made of material that has a low binding affinity for nucleic acids. Suitable materials include, but are not limited to, plastics such as polypropylene, polystyrene, and polyethylene, among others. In some embodiments, first hollow body 1 and second hollow body 2 are made of metal or composite material. In some embodiments, inner surfaces 140, 240 are coated with one or more substances that lowers the binding affinity of the surfaces for nucleic acids.

In some embodiments, second hollow body 2 comprises an upper region 232, an intermediate region 234, and a terminal region 236. In some embodiments, terminal region 236 is tapered. In at least one embodiment, the taper of terminal region 236 is configured to facilitate passage of fluid sample 3 out of second hollow body 2.

In several embodiments, second hollow body 2 has a tab 260 that extends from outer surface 230. In some embodiments, tab 260 is located in upper region 232. Tab 260 has an upper surface 262. In some embodiments, upper surface 262 is substantially co-planar with inlet opening 201. In several embodiments, upper surface 262 is sufficiently dimensioned to serve as a platform for labeling second hollow body 2. In at least one embodiment, upper surface 262 is between about 1 mm to about 5 mm wide and about 1 mm to about 5 mm long. In some embodiments, a label 264 is affixed to upper surface 262. In several embodiments, upper surface 262 is marked by any suitable means including ink, or etching. In at least one embodiment, label 264 or the marking of upper surface 262 denotes the identity (e.g., the source patient) of the fluid sample 3 that has been passed through second hollow body 2. In some embodiments, label 264 or marking of upper surface 262 encodes a bar code (e.g., a 2D or 3D bar code). In several embodiments, RFID tags or other identifiers may be used to denote the patient identity from which the sample was obtained.

In several embodiments, upper region 232 of second hollow body 2 is configured to functionally communicate with terminal region 136 of first hollow body 1. First hollow body 1 and second body 2 may functionally communicate by any number of ways including but not limited to mating screw threads, an interference fit, and a compression fitting. In some embodiments, terminal region 136 of first hollow body 1 is configured to fit inside upper region 232 of second hollow body 2. In some embodiments, upper region 232 of second hollow body 2 is configured to fit inside terminal region 136 of first hollow body 1. In some embodiments, at least a portion of outer surface 130 is surrounded by at least a portion of inner surface 240. In some embodiments, at least a portion of outer surface 230 is surrounded by at least a portion of inner surface 140. In some embodiments, outlet diameter 112 is smaller than inlet diameter 211.

In some embodiments, first hollow body 1 has at least one pin 150 that protrudes from outer surface 130 of terminal region 136, and second hollow body 2 has at least one channel 250 in upper region 232 of second hollow body 2 (see e.g., FIG. 3). In at least one embodiment, pin 150 is configured to reversibly cooperate with channel 250. Channel 250 has a longitudinal portion 252, a transverse portion 254, and a retrograde portion 256. In some embodiments, first hollow body 1 is coupled to second hollow body 2 by sliding pin 150 into longitudinal portion 252 of channel 250. First hollow body 1 and second hollow body 2 are positioned to allow pin 150 to reach transverse portion 254 of channel 250. Second hollow body 2 is then rotated to bring pin 150 into transverse portion 254 until pin 150 lines up with retrograde portion 256 of channel 250. The compressive force between first hollow body 1 and second hollow body 2 is then reduced, allowing pin 150 to slide into retrograde portion 256, thereby securing a coupling between first hollow body 1 and second hollow body 2. In some embodiments, second hollow body 2 is removed from first hollow body 1 by squeezing the two hollow bodies together and allowing pin 150 to retrace channel 250.

In some embodiments, the at least one channel 250 in upper region 232 of second hollow body 2 comprises a longitudinal portion 252 and a transverse portion 254. In some embodiments, first hollow body 1 is coupled to second hollow body 2 by sliding pin 150 into longitudinal portion 252 of channel 250. First hollow body 1 and second hollow body 2 are positioned to allow pin 150 to reach transverse portion 254 of channel 250. Second hollow body 2 is then rotated to bring pin 150 into transverse portion 254 thereby securing a coupling between first hollow body 1 and second hollow body 2. After processing, second hollow body 2 is removed from first hollow body 1 by rotating the two hollow bodies in the opposite direction and allowing pin 150 to retrace channel 250, thereby allowing the first and second hollow bodies to disengage. In several embodiments, the first and second hollow body are configured to reversible interact in a manner that allows their decoupling to occur without requiring second hollow body to be re-passed through the interior of first hollow body. That is, certain devices may allow interaction of the first and second bodies by virtue of the second hollow body being inserted into, and partially through, the first hollow body (e.g., the second body nests inside the first body). While this provides some advantages (e.g., security of the interaction during centrifugation or other handling) this then requires the second hollow body to retrace its path (e.g., an upward path) through the first hollow body to disengage the two. This presents a potential issue with respect to cross contamination. Advantageously, in several embodiments, the second hollow body of the devices disclosed herein can be decoupled from the first hollow body without requiring the second hollow body to pass through the first hollow body. In several embodiments, this greatly reduces the risk for contamination of the second hollow body, but the reversible interaction between the two bodies is sufficient to maintain a secure interaction during centrifugation (or other handling).

In several embodiments, capture material 4 is made from any suitable material that can retain the target component being extracted from fluid sample 3. In several embodiments, the material used for capture material 4 is optimized to balance the attractive nature of the material for the target component and the ability of the material to release the target component under appropriate conditions.

In some embodiments, capture material 4 is optionally modified to tailor the profile of target components retained by capture material 4. In some embodiments, capture material 4 is electrocharged (e.g., electrostatically charged), coated with hydrophilic or hydrophobic materials, chemically modified, and/or biologically modified. In several embodiments, the zeta potential of capture material 4 is used as a basis for modification (e.g., electrostatic charging) of the material. In some embodiments, capture material 4 (based on its zeta potential) does not require modification. In some embodiments, capture material 4 is modified by attaching a nucleotide sequence to the surface of capture material 4. In some embodiments, a protein is attached to the surface of capture material 4. In some embodiments, biotin or streptavidin is attached to the surface of capture material 4. In some embodiments, an antibody or antibody fragment is attached to capture material 4. Any of such embodiments can be employed to advantageously increase the efficiency of capture of a target.

In some embodiments, differential capture of vesicles is achieved based on the surface expression of protein markers and a complementary agent on capture material 4 which identifies that marker (e.g., an antibody that recognizes an antigen on a particular vesicle). In some embodiments, the markers are unique vesicle proteins or peptides. In some disease states, the markers may also comprise certain vesicle modifications, which, in some embodiments, are used to isolate particular vesicles. In such embodiments, capture material 4 may be configured in a manner which allows for specific recognition of the vesicle modification. Modification of the vesicles may include, but are not limited to the addition of lipids, carbohydrates, and other molecules such as acylated, formylated, lipoylated, myristolylated, palmitoylated, alkylated, methylated, isoprenylated, prenylated, amidated, glycosylated, hydroxylated, iodinated, adenylated, phosphorylated, sulfated, and selenoylated, ubiquitinated. In some embodiments, capture material 4 is configured to recognize vesicle markers comprising nonproteins such as lipids, carbohydrates, nucleic acids, RNA, mRNA, siRNA, microRNA, DNA, etc.

In some embodiments, the interactions between vesicles and capture material 4 are based on electrostatic interaction, hydrophobic interaction, van der Waals force, or a combination of these interactions. Thus, the biochemical makeup of the sample comprising the vesicles can alter these forces, possibly to a degree that significantly hampers the capture efficiency.

In several embodiments, a target range for capture conditions that the vesicles are exposed to when passed over/through the capture materials comprise between about 1 mM and about 1000 mM monovalent cation (e.g., sodium and/or potassium), including ranges having a lower concentration of about 10 mM, about 20 mM, about 30 mM, about 40 mM, about 50 mM, about 60 mM, about 70 mM, about 80 mM, about 90 mM or about 100 mm, about 110 mM, about 120 mM, about 130 mM, about 140 mM, about 150 mM, about 160 mM, about 170 mM, about 180 mM, about 190 mM, about 200 mM (and any concentration therebetween) and upper concentrations of about 500 mM, about 600 mM, about 700 mM, about 800 mM, and about 900 mM (and any concentration therebetween). Thus, in several embodiments the concentration ranges are from about 20 mM to about 900 mM, from about 20 mM to about 800 mM, from about 30 mM to about 700 mM, and from about 40 mM to about 600 mM, and overlapping ranges thereof. In conjunction with those conditions, the pH is adjusted, in several embodiments, from about 4, about 5, or about 6 to about 9 or about 10 (or pH values between those listed). Thus, depending on the embodiment, pH ranges include from about 4 to about 10, from about 5 to about 9, and from about 6 to about 9.

In some embodiments, the materials used for capture material 4 comprise materials that inhibit the capture of vesicles. Thus, in several embodiments, capture material 4 is pre-treated to remove such inhibitory materials in advance of using the capture material to capture the vesicles. For example, high concentrations of proteins such as albumin may lower the capture efficiency of vesicle capture. In such cases, albumin can be removed by various techniques, such as, for example, passing materials or solutions through or over capture material 4, the materials or solutions comprising a compound (e.g., Blue Trisacryl M resin) with a greater affinity for the albumin than the albumin has for capture material 4. The techniques used to remove contaminants may also include heating, acid bath, basic bath, ultrasonic cleaning, and the like.

In several embodiments, it is advantageous to adjust the biochemical characteristics of fluid sample 3 to preferred ranges (e.g., salt concentration, pH, etc.) prior to attempting to capture the vesicles. In several embodiments, a buffer solution such as phosphate buffer saline (PBS) or HEPES buffer is used. In several embodiments, the pH of such buffers ranges from a pH of about 6 to about 9. In several embodiments, the concentration of monovalent cations such as sodium and potassium is greater than about 50 mM, greater than about 60 mM, greater than about 70 mM, greater than about 80 mM, greater than about 90 mM, greater than about 100 mM, greater than about 200 mM, and sometimes may require even greater concentrations, depending on the embodiment. In several embodiments, the end result of the mixture of the urine and buffer solution is between about 20 mM and about 600 mM monovalent cation, such as sodium and potassium, and between about pH 6 and about pH 9. Capturing vesicles can then be performed as discussed in more detail below, and analysis performed as described below.

In several embodiments, capture material 4 is made of glass-like material. In some embodiments, capture device 100 includes a filter material 5 (shown in FIG. 2) that is configured to filter fluid sample 3 before fluid sample 3 passes through capture material 4. In some embodiments filter material 5 is placed in second hollow body 2 between capture material 4 and inlet opening 201. In some embodiments, filter material 5 is placed in first hollow body 1 between intermediate region 136 and outlet opening 102. In several embodiments, however, no filter material is used.

In several embodiments, combinations of filter material 5 and capture material 4 are used. In some embodiments, capture material 4 comprises a plurality of layers of material. In several embodiments, capture material 4 comprises at least a first layer and a second layer of glass fiber. In some embodiments, fluid sample 3 is passed through filter material 5 to capture components that are about 1.6 microns or greater in diameter. In some embodiments, fluid sample 3 is passed through capture material 4 so as to capture vesicles having a minimum size from about 0.6 microns to about 0.8 microns in diameter, and having a maximum size of less than about 1.6 microns. In several embodiments, the retention rate of capture material 4 is greater than about 50%, about 75%, about 90%, or about 99% for vesicles having a diameter of from about 0.6 microns to about 1.5 microns in diameter. In at least one embodiment, capture material 4 captures vesicles sized from about 0.7 microns to about 1.6 microns in diameter. In at least one embodiment, capture material 4 captures exosomes or other vesicles ranging in size from about 0.020 microns to about 1.0 microns.

In several embodiments, capture material 4 comprises combinations of glass-like and non-glass-like materials. For example, in one embodiment, a non-glass-like material comprising nitrocellulose is used. In some embodiments, capture material 4 comprises glass-like materials, which have a structure that is disordered, or "amorphous" at the atomic scale, such as plastic or glass. Glass-like materials include, but are not limited to, glass beads or fibers, silica beads (or other configurations), nitrocellulose, nylon, polyvinylidene fluoride (PVDF) or other similar polymers, metal or nano-metal fibers, polystyrene, ethylene vinyl acetate or other co-polymers, natural fibers (e.g., silk), alginate fiber, or combinations thereof. Other suitable materials for capture material 4 include zeolite, metal oxides or mixed metal oxides, aluminum oxide, hafnium oxide, zirconium oxide, or combinations thereof.

In some embodiments, vesicles are retained in capture material 4 by virtue of the vesicle having physical dimensions that prohibit the vesicle from passing through the spaces of capture material 4 (e.g., physical retention based on size). In some embodiments, vesicles are retained in capture material 4 by bonding forces between the vesicle and capture material 4. In some embodiments, vesicles form antigen-antibody bonds with capture material 4. In several embodiments, vesicles form hydrogen bonds with capture material 4. In some embodiments, van der Waals forces form between the vesicle and capture material 4. In some embodiments, nucleotide sequences of the vesicle bind to nucleotide sequences attached to capture material 4.

Figure 5:
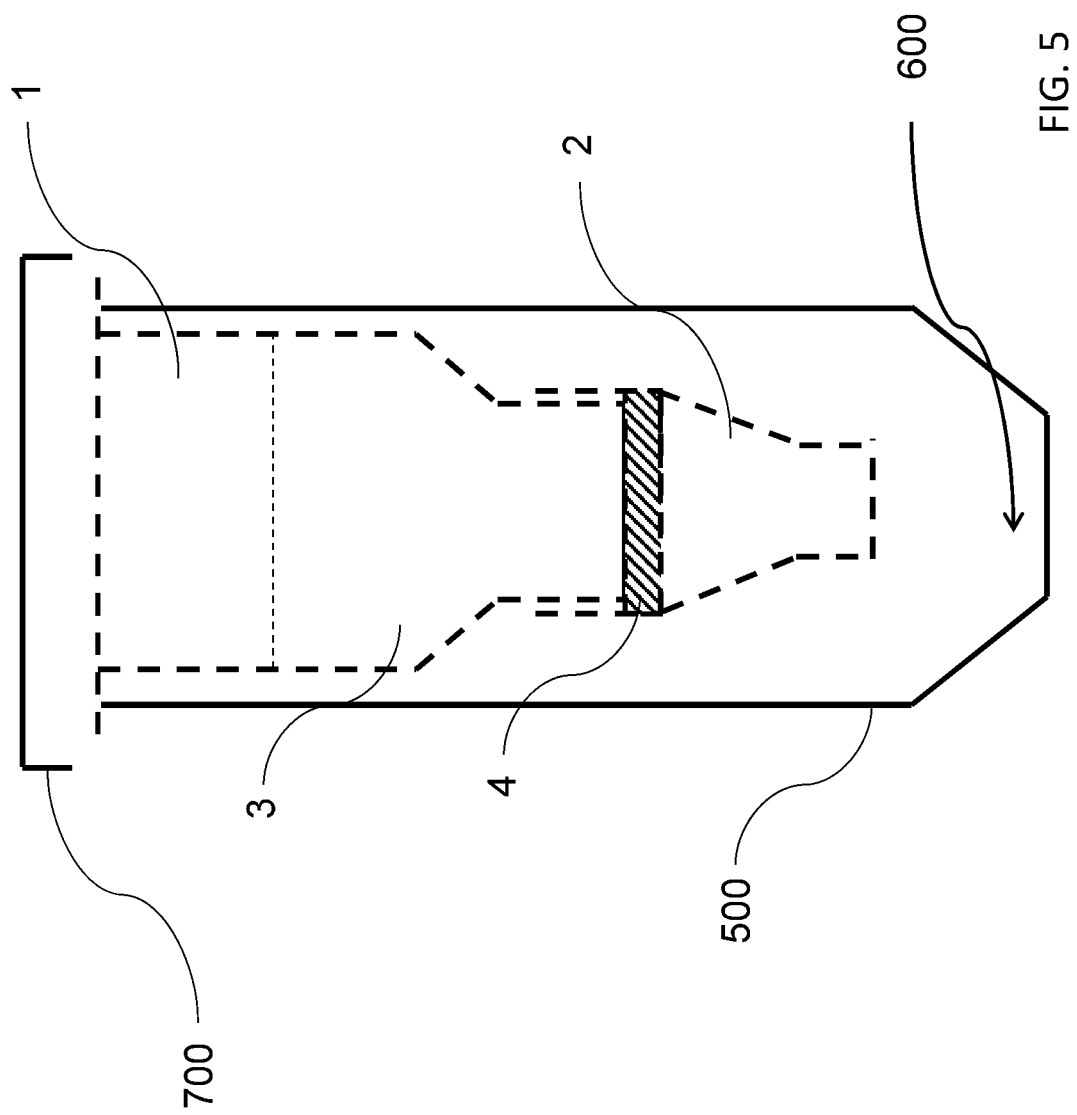
FIG. 5 is a cross-section view of microvesicle capture system as disclosed herein.

In several embodiments, capture device 100 is used in conjunction with a receiving vessel 500 (see FIG. 5) that receives fluid sample 3 in a receiving compartment 600 after fluid sample 3 has passed through capture device 100. In some embodiments, the receiving vessel also includes a cap 700, to secure the capture device 100 within the receiving vessel 500 during processing. In several embodiments, the cap is a press-fit cap, while in other embodiments the cap comprises a screw-fit cap. In several embodiments, the receiving vessel comprises a centrifuge tube, thus, in some embodiments, first hollow body 1 and second hollow body 2 are sized to fit within a receiving vessel/centrifuge tube. In some embodiments, collar 105 serves as a means for holding capture device 100 in a fixed position relative to the receiving vessel. In several embodiments, capture device 100 and collar 105 are sized to permit use of capture device 100 with a receiving vessel such as a 10 mL, 12 mL, 15 mL, 30 mL, 50 mL, 175 mL, or 225 mL centrifuge tube, though centrifuge tubes of other sizes and capacities are also contemplated. In some such embodiments, collar 105 is sized to fit over the mouth of the centrifuge tube without obstructing the function of the threaded cap of the centrifuge tube. In several embodiments, capture device 100 is placed within a centrifuge tube, and centrifugal force is applied to drive fluid sample 3 from first hollow body 1 through capture material 4 and into second hollow body 2.

In some embodiments, capture device 100 is sized so that outlet opening 202 of second hollow body 2 does not contact fluid sample 3 after fluid sample 3 has passed through capture device 100 and accumulated in the receiving vessel. In some embodiments, the volume capacity of the receiving vessel is greater than the volume capacity of capture device 100 by about 2-fold, by about 3-fold, by about 4-fold, or by about 5-fold.

In some embodiments, capture device 100 has a volume sufficient to receive the entire fluid sample 3 and other reagents to facilitate binding of nucleic acids to capture material 4. In some embodiments, capture device 100 is sized to accommodate a volume of between about 1 mL and 1000 mL, including between about 1 mL and 100 mL, between about 5 mL and 50 mL, between about 10 mL and 20 mL, and any volumes between those ranges. In some embodiments, capture device 100 accommodates a volume of about 15 mL.

In some embodiments, the capacity of first hollow body 1 is greater than the capacity of second body 2 by about 100-fold, or by about 50-fold, or by about 20-fold, or by about 10-fold, or by about 5-fold. In some embodiments, the capacity of first hollow body 1 is about the same as the capacity of second hollow body 2.

In many embodiments, the dimensions of capture material 4 are optimized to balance having sufficient capture material 4 to adequately capture a target from sample 3 while also allowing a small volume of liquid (e.g., microliter scale) to be used to elute the bound target components. Reducing the volume of recovery liquid allows, in certain advantageous embodiments, target components to be extracted at higher concentrations. In some embodiments, the volume of capture device 100 is greater than the volume of capture material 4 by about 1000-fold, by about 500-fold, by about 300-fold, or by about 100-fold. In embodiments where the material of capture material 4 includes interstitial spaces, the meaning of the phrase "volume of capture material 4" shall be taken to include the volume of these interstitial spaces. In several embodiments, the elution volume ranges from about 5 to about 500 microliters, including about 5 microliters to about 10 microliters, about 10 microliters to about 20 microliters, about 20 microliters to about 50 microliters, about 50 microliters to about 100 microliters, about 100 microliters to about 150 microliters, about 150 microliters to about 200 microliters, about 200 microliters to about 300 microliters, about 300 microliters to about 400 microliters, about 400 microliters to about 500 microliters, and overlapping ranges therebetween.

In some embodiments, capture material 4 is cuboidal. In some embodiments capture material 4 is wafer-shaped, spherical, or some combination thereof. In some embodiments capture material 4 has a surface area to thickness ratio of about 50:1, about 25:1, about 10:1, about 5:1, or about 3:1. In some embodiments, capture material 4 is a cylindrical wafer having a diameter to length ration of about 20:1, about 10:1, about 5:1, or about 2:1. In at least one embodiment, capture material 4 is cylindrical and has a diameter of about 9 mm and a thickness of about 1 mm.

In some embodiments, a fluid sample is passed through the device by way of application of positive pressure. For example, in some embodiments, the first hollow body 1 is configured to receive a syringe plunger, which, when depressed toward second hollow body, provides a positive pressure that drives fluid sample 3 through capture device 100. In some embodiments, a fluid sample is passed through the device by way of application of negative pressure. For example, in some embodiments, the second hollow body is adapted to reversibly connect to a vacuum source, such as a vacuum manifold, thereby allowing application of a negative pressure that drives fluid sample 3 through capture device 100. In some embodiments employing a receiving vessel, the receiving vessel is configured to pass a negative (or positive, depending on the embodiment) pressure to the capture device, thereby allowing the fluid sample to be passed through the capture device. However, in several embodiments, no specific positive or negative pressure is applied. For example, in several embodiments, centrifugal forces are applied to drive fluid sample 3 through capture device 100. Gravitational flow may also be used, in several embodiments.

In some embodiments, terminal region 236 of second hollow body 2 is sized to fit within a well of a standard multi-well plate. In several embodiments, terminal region 236 is sized to fit within a well of a standard 6-well plate, or a standard 12-well plate, or a standard 24-well plate, or a standard 96-well plate, or a standard 384-well plate, or a standard 1536-well plate, etc. Such plates are commercially available from various manufacturers, including but not limited to, Corning, Nunc, Fisher, BD Biosciences, etc. In several embodiments, the plates have well dimensions that are shown in Table 1.

TABLE 1

Example Microplate Dimensions for Use with Capture Systems

| Number of Wells | Plate Length (mm) | Plate Width (mm) | Well Diameter (mm, at top of well) |
|---|---|---|---|
| 6 | 127.76 | 85.47 | 35.43 |
| 12 | 127.89 | 85.6 | 22.73 |
| 24 | 127.89 | 85.6 | 16.26 |
| 48 | 127.89 | 85.6 | 11.56 |
| 96 | 127.8 | 85.5 | 6.86 |

In some embodiments, tab 260 of second hollow body 2 extends over at least a portion of a neighboring well of a multi-well plate when second hollow body 2 interacts with a first well of the multi-well plate. In at least one embodiment, tab 260 is configured to allow half of the wells of a multi-well plate to be occupied at a time by second hollow bodies 2 without tabs 260 overlapping with one another. In some embodiments, second hollow body 2 has a protrusion 270 that interacts with a wall of a well of a multi-well plate and secures second hollow body 2 to a well of the multi-well plate. In several embodiments, tab 260 is dimensioned so that each well of a multi-well plate can be used to receive a sample.

In several embodiments, a method for isolating a biomarker comprises taking a fluid sample 3 from a patient, passing the fluid sample 3 through capture material 4, removing non-vesicle material from capture material 4, and lysing the vesicles in or on capture material 4 with a lysis buffer, thereby isolating a biomarker from the vesicles. In some embodiments, the biomarker is selected from the group consisting of RNA, DNA, protein, and carbohydrate. In several embodiments, the RNA is of a type selected from the group consisting of mRNA, miRNA, rRNA, tRNA, and vRNA.

In some embodiments, capture device 100 is placed within a centrifuge tube, and collar 105 holds capture device 100 in a fixed position relative to the centrifuge tube. Fluid sample 3 is loaded into capture device 100 before or after placing capture device 100 within the centrifuge tube. Capture device 100 is subjected to centrifugation. The centrifuge tube serves as a receiving vessel and receives fluid sample 3 after it has passed through capture device 100. In some embodiments, low-speed centrifugation is used to drive fluid sample 3 through capture device 100.

In some embodiments, a kit is provided for extracting target components from fluid sample 3. Kits often allow better management of quality control and better consistency in results. In some embodiments, a kit comprises a capture device 100 and additional items useful to carry out methods disclosed herein. In some embodiments, a kit comprises reagents selected from the group consisting of lysis buffers, chaotropic reagents, washing buffers, alcohol, detergent, or combinations thereof. In some embodiments, kit reagents are provided individually or in storage containers. In several embodiments, kit reagents are provided ready-to-use. In some embodiments, kit reagents are provided in the form of stock solutions that are diluted before use. In some embodiments, a kit comprises plastic parts that are useful to carry out methods herein disclosed. In some embodiments, a kit comprises plastic parts selected from the group consisting of racks, centrifuge tubes, vacuum manifolds, and multi-well plates. Instructions for use are also provided, in several embodiments.

EXAMPLES

Example 1—Effect of pH/Salt Concentration on Exosome Capture

The impacts of various characteristics of a biological sample were evaluated with respect to the efficacy of exosome capture. Urine samples collected from four healthy donors were centrifuged at 800×g for 15 min and the supernatants were collected. 4.5 mL of urine supernatant from each subject was mixed with different volumes of concentrated buffer solution prior to processing. Samples were processed by the collection device disclosed herein. In brief, the samples were added to the first body, which was connected to the second body. The first and second bodies were placed inside a 50 mL conical centrifuge tube (receiving vessel) and centrifuged at 2,000×g 10 min to capture exosomes and microvesicles (EMV) on a capture filter within the second body. Thereafter, the first and second bodies were removed from the receiving vessel and the second body was disengaged from the first body. The second body was placed with its outlet portion in a well of a multiwell microplate. After lysing the captured EMV by a lysis buffer (37° C. 10 min), the lysates were transferred to an oligo(dT) immobilized microplate (Hitachi Chemical Research Center, Inc.) for mRNA isolation. Several kidney-related genes including housekeeping mRNAs were quantified by real-time RT-PCR. For protocol comparison, a standard ultracentrifugation protocol was used for exosome isolation. The 800×g supernatants were centrifuged at 100,000×g for 1 hour and the EMV pellets were collected. After lysing the EMV by a lysis buffer, the lysates were transferred to an oligo(dT) immobilized microplate and processed for mRNA isolation and real-time RT-PCR.

Figure 6:
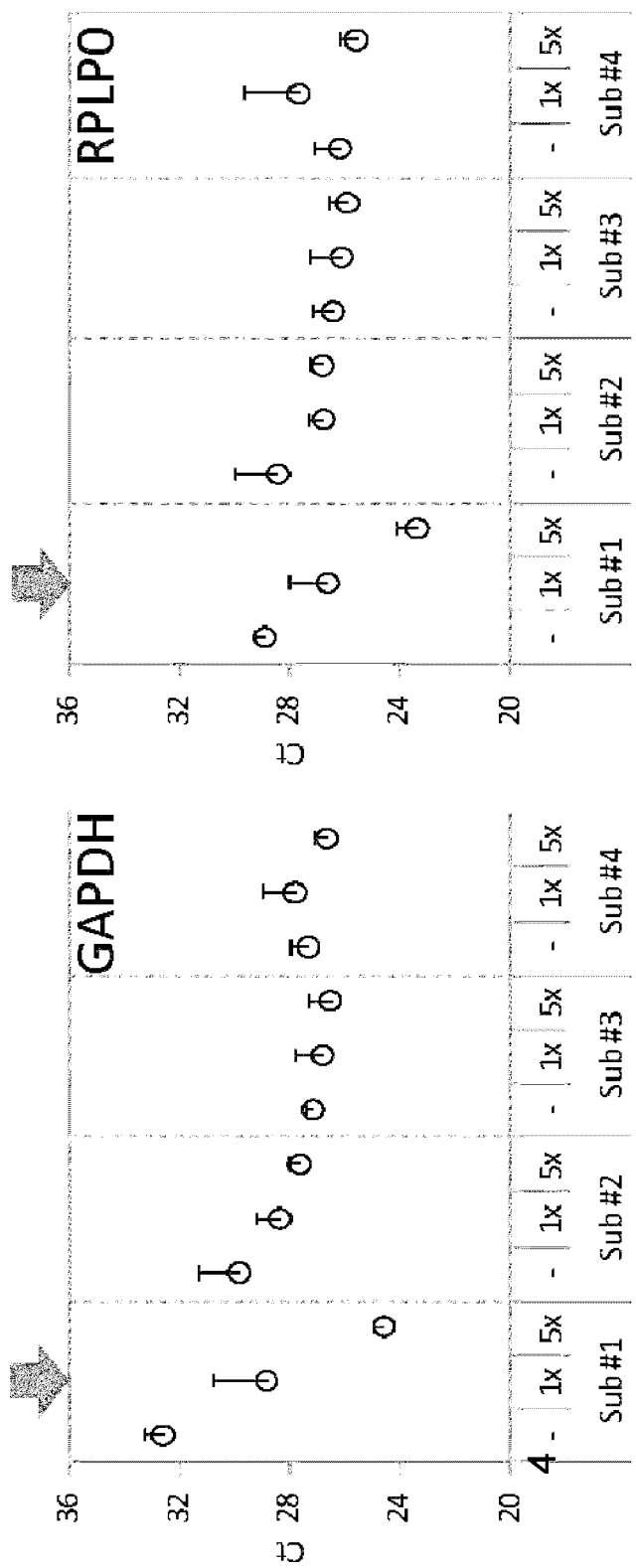
FIG. 6 depicts data related to the exosome capture efficiency after adjusting the salt and pH of urine samples

As shown in FIG. 6 addition of a buffer solution to adjust the pH and the salt concentration of urine sample improve the efficiency of exosome capture using the device is disclosed herein. FIG. 6, as depicted by the arrows, improve the assay sensitivity of urine samples collected from subject #1 (based on expression of GAPDH and RPLPO housekeeping genes) but do not adversely impact sensitivity of the samples from other subjects.

Example 2—Filter Based Exosome Capture Compared to Standard Ultracentrifugation

Many commonly used protocols and play ultracentrifugation to capture exosome from biological fluids. However, as discussed above, ultracentrifugation can be cost intensive. On exosome capture device, as disclosed herein, was used to process 0.1 to 10 mL urine samples. Urine samples were also processed to capture exosomes using established ultracentrifugation methods. Identical mRNA isolation and PCR protocols were then used.

Figure 7:
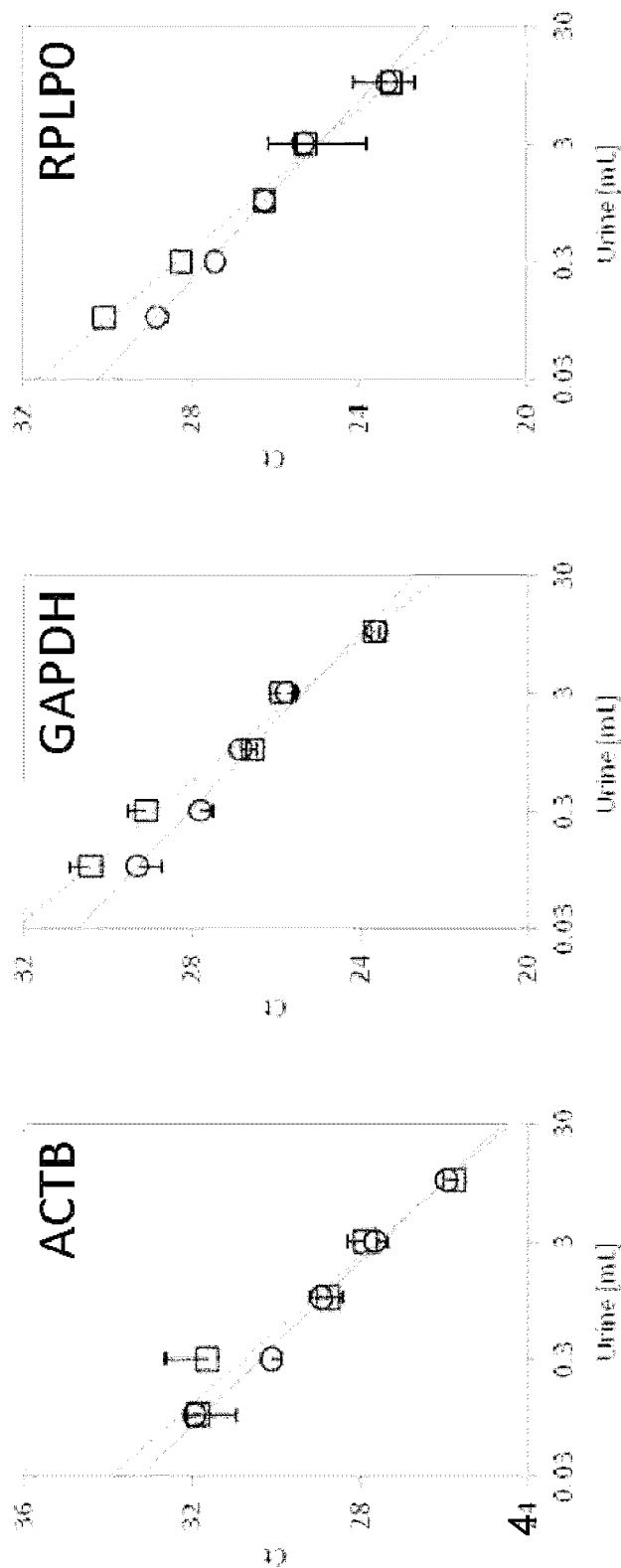
FIG. 7 depicts data related to the efficacy of exosome capture with the devices disclosed herein as compared to ultracentrifugation-based isolation.

FIG. 7 shows the results of PCR application of three housekeeping genes (beta actin, GAPDH and RPLPO) based on isolation using the disclosed exosome capture device (open circles) or ultracentrifugation of (open squares). A high degree of correlation was detected between both methods, thereby indicating that the exosome capture devices disclosed herein are effective at capturing exosome and maintaining the mRNA within those exosomes.

Figures 1, 8:
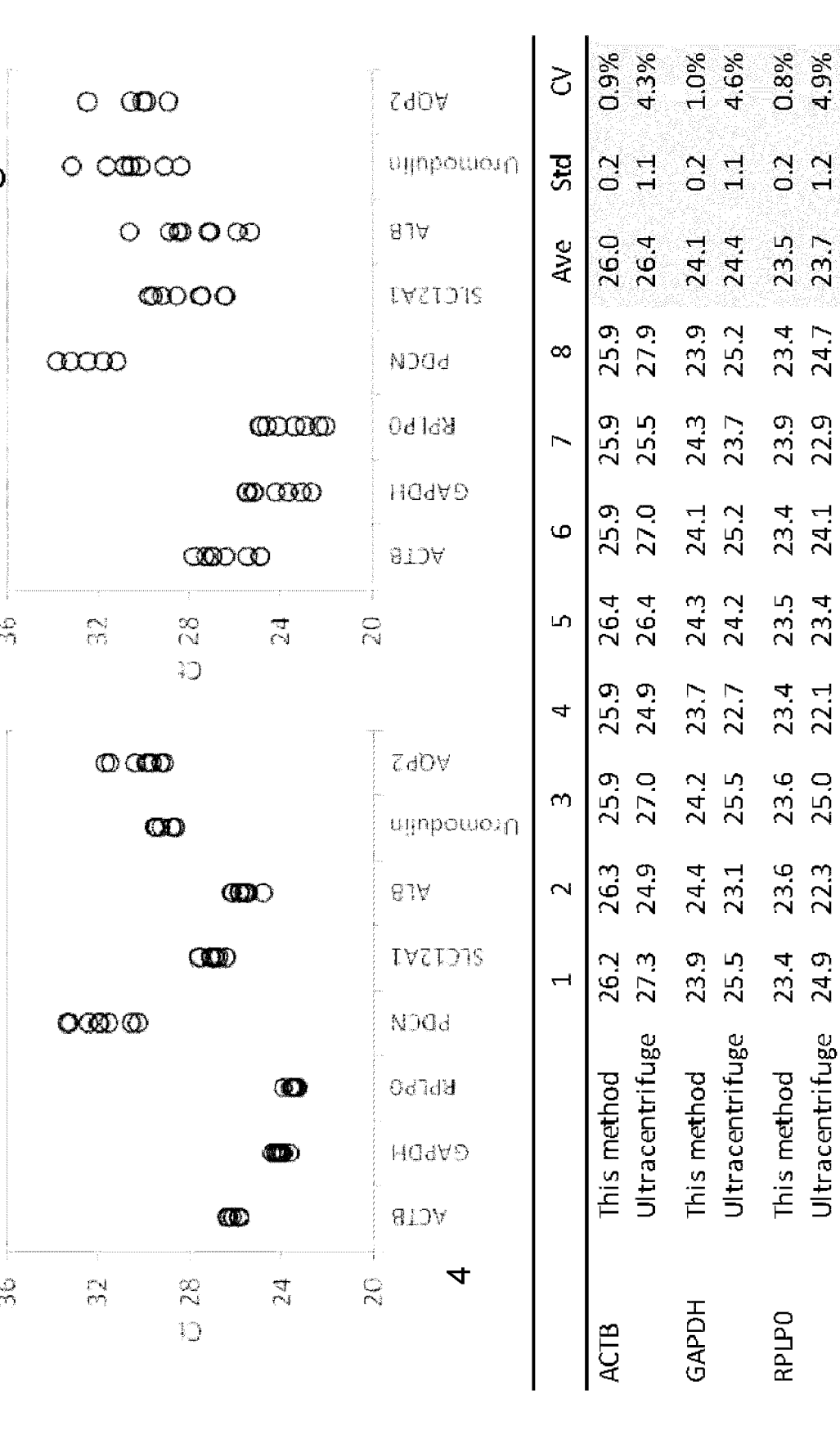

FIG. 8 shows additional data related to the intra-assay variation when exosome capture using the devices disclosed herein was compared with ultracentrifugation-based methods. As shown in FIG. 8 and Table 2, highly similar mRNA expression profiles were detected using either method, thus indicating that exosome capture using the devices disclosed herein provides reproducible and accurate mRNA results. Moreover, these data show a significantly reduced intra-assay variation when using the exosome capture devices disclosed herein. As such gene expression analysis using these devices can achieve higher degrees of accuracy and reduce the risk of false positive results based on data variability.

TABLE 2

Intra-assay Variation Using Exosome Capture Devices

| Gene | Method | Run 1 | Run 2 | Run 3 | Run 4 | Run 5 | Run 6 | Run 7 | Run 8 | Avg. | Std. Dev | CV (%) |
|---|---|---|---|---|---|---|---|---|---|---|---|---|
| Beta-Actin | Device | 26.2 | 26.3 | 25.9 | 25.9 | 26.4 | 25.9 | 25.9 | 25.9 | 26.0 | 0.2 | 0.9 |
|  | Ultra | 27.3 | 24.9 | 27.0 | 24.9 | 26.4 | 27.0 | 25.5 | 27.9 | 26.4 | 1.1 | 4.3 |
| GAPDH | Device | 23.9 | 24.4 | 24.2 | 23.7 | 24.3 | 24.1 | 24.3 | 23.9 | 24.1 | 0.2 | 1.0 |
|  | Ultra | 25.5 | 23.1 | 25.5 | 22.7 | 24.2 | 25.2 | 23.7 | 25.2 | 24.4 | 1.1 | 4.6 |
| RPLP0 | Device | 23.4 | 23.6 | 23.6 | 23.4 | 23.5 | 23.4 | 23.9 | 23.4 | 23.5 | 0.2 | 0.8 |
|  | Ultra | 24.9 | 22.3 | 25.0 | 22.1 | 23.4 | 24.1 | 22.9 | 24.7 | 23.7 | 1.2 | 4.9 |
| PDCN | Device | 30.3 | 32.0 | 33.3 | 31.9 | 33.4 | 20.6 | 32.4 | 31.6 | 31.9 | 1.1 | 3.5 |
|  | Ultra | 33.9 | 31.2 | 40.0 | 31.8 | 32.5 | 40.0 | 33.2 | 40.0 | 35.3 | 4.0 | 11.2 |
| SLC12A1 | Device | 27.1 | 27.7 | 26.4 | 26.9 | 27.1 | 26.8 | 27.6 | 26.9 | 27.1 | 0.4 | 1.5 |
|  | Ultra | 29.8 | 26.5 | 28.6 | 26.4 | 27.5 | 29.2 | 27.5 | 29.6 | 28.1 | 1.4 | 4.8 |
| ALB | Device | 25.9 | 26.2 | 24.9 | 25.5 | 25.9 | 25.7 | 26.2 | 25.5 | 25.7 | 0.4 | 1.7 |
|  | Ultra | 28.9 | 25.9 | 30.6 | 25.4 | 27.1 | 28.5 | 27.2 | 28.3 | 27.7 | 1.7 | 6.1 |

TABLE 2-continued

Intra-assay Variation Using Exosome Capture Devices

| Gene | Method | Run 1 | Run 2 | Run 3 | Run 4 | Run 5 | Run 6 | Run 7 | Run 8 | Avg. | Std. Dev | CV (%) |
|---|---|---|---|---|---|---|---|---|---|---|---|---|
| Uromodulin | Device | 29.3 | 29.5 | 28.8 | 29.5 | 28.6 | 28.7 | 29.6 | 29.6 | 29.2 | 0.4 | 1.4 |
|  | Ultra | 30.8 | 28.4 | 33.1 | 29.1 | 30.2 | 30.6 | 30.9 | 31.6 | 30.6 | 1.5 | 4.8 |
| AQP2 | Device | 30.4 | 31.7 | 29.8 | 29.3 | 31.5 | 29.7 | 29.1 | 29.9 | 29.9 | 1.0 | 3.2 |
|  | Ultra | 40.0 | 30.1 | 32.5 | 29.0 | 30.6 | 40.0 | 29.9 | 40.0 | 40.0 | 5.1 | 14.9 |

Figure 9:
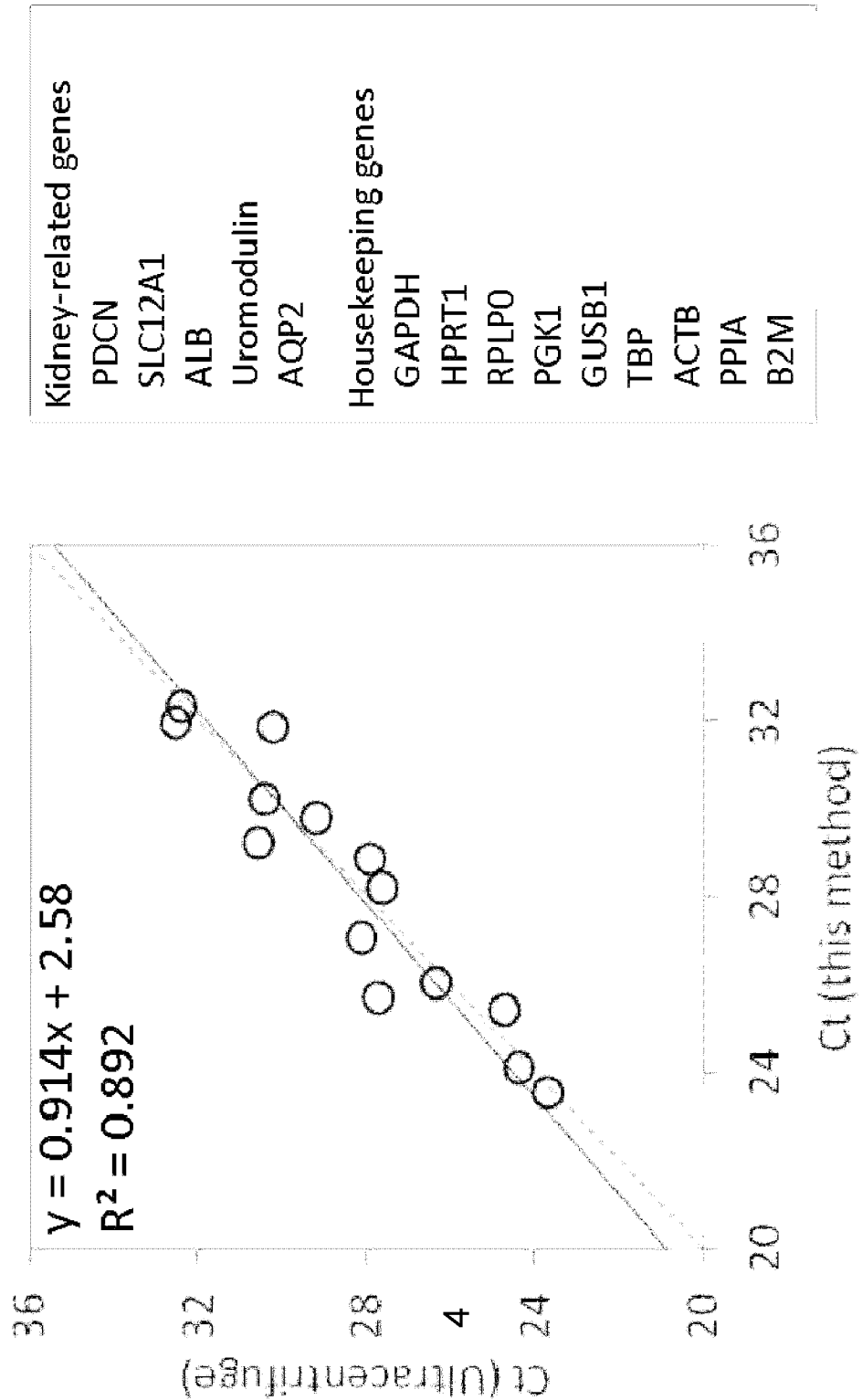
FIG. 9 depicts the comparison of an RNA profile detected after exosome capture using the devices disclosed herein as compared to ultracentrifugation-based isolation.

An additional experiment was performed to determine the similarity in mRNA profile when exosomes were captured using the devices disclosed herein or using ultra centrifugation based protocols. Certain kidney related genes, as well as a variety of housekeeping genes were amplified from urine samples (10 mL) processed through the devices disclosed herein or by ultracentrifugation. As shown in FIG. 9 very similar expression profiles resulted, regardless of the method employed. These data, in conjunction with the data above relating to reduced intra-assay variability indicate that the devices disclosed herein can result in highly accurate mRNA expression data.

Example 3—Urine Exosome Monitoring

Figure 10A:
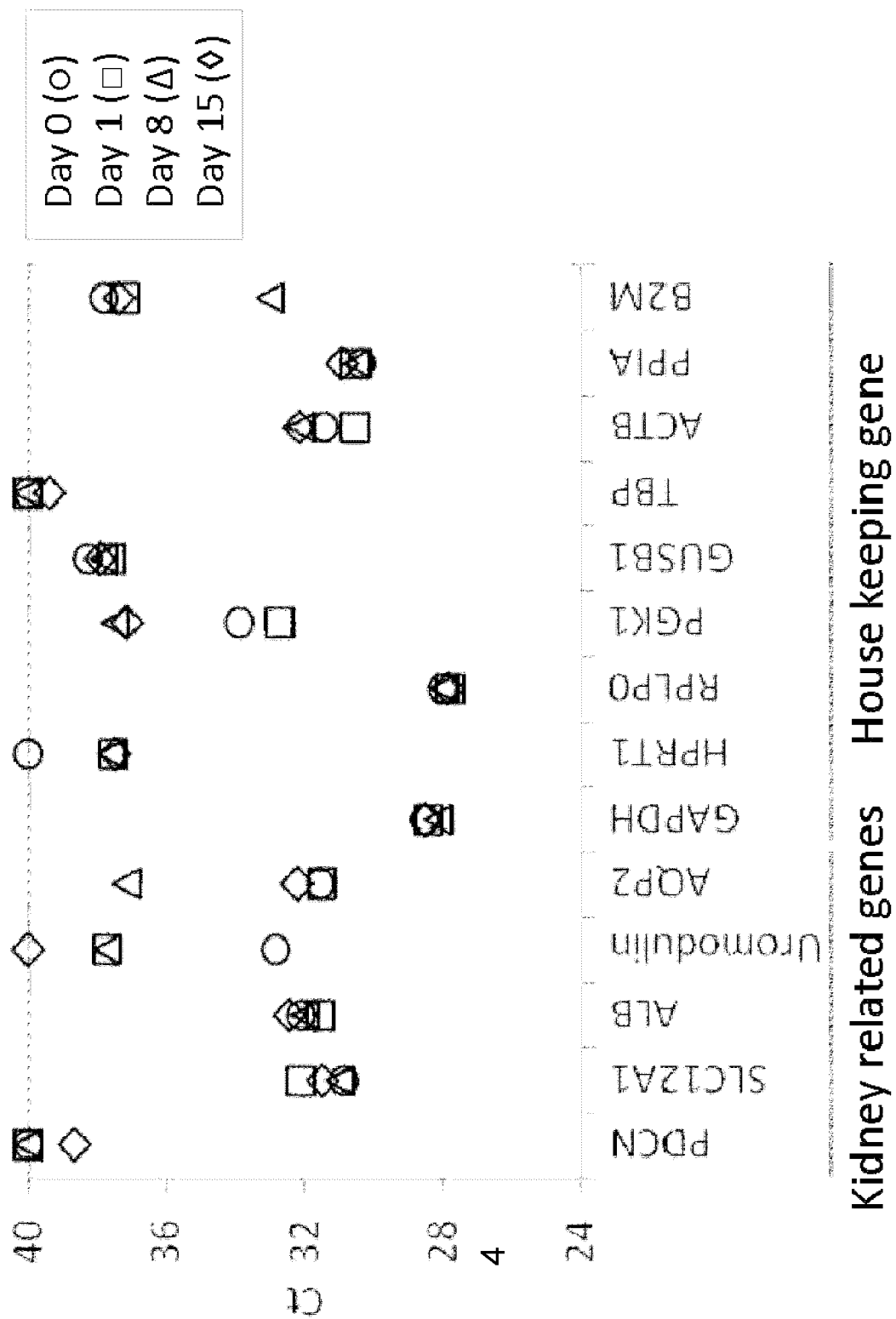
FIG. 10A depicts data related to the similar RNA profile detected from a 12-hr urine sample when analyzed after capture of exosomes using the devices disclosed herein as compared to ultracentrifugation-based isolation.
Figure 10B:
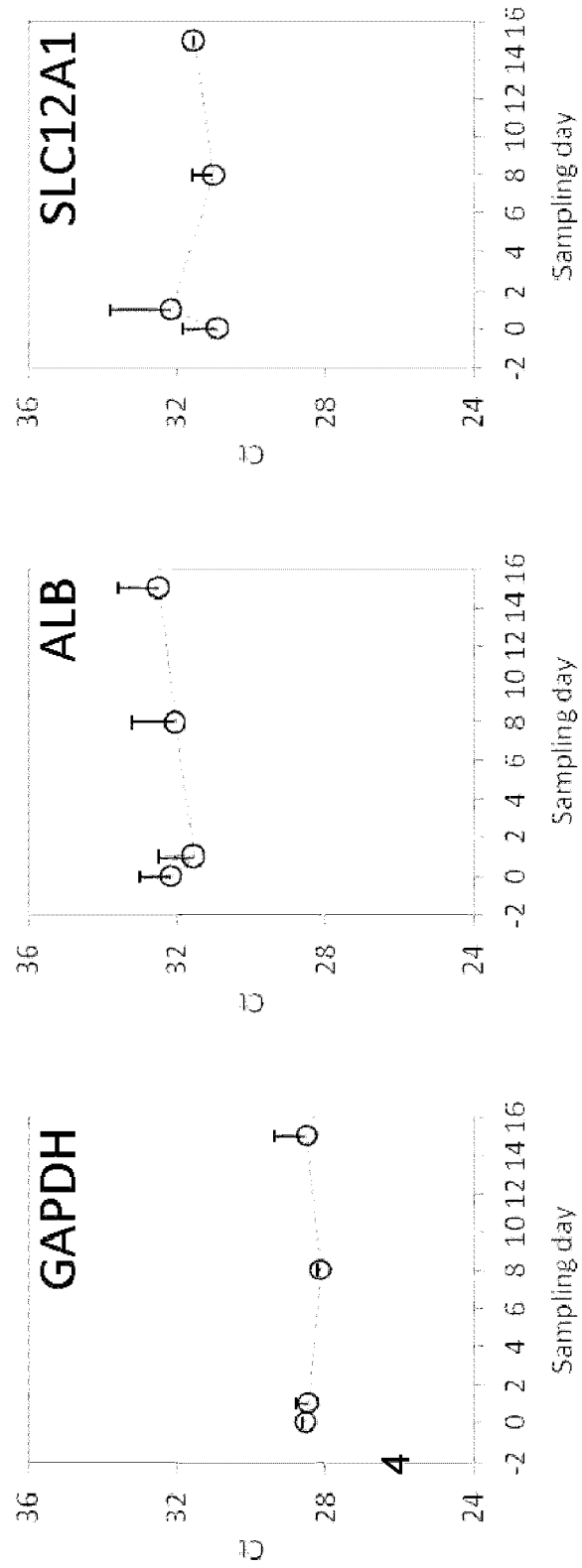
FIG. 10B depicts data related to the consistency of RNA detection over a two-week time period when exosomes recaptured using the devices disclosed herein.

The exosome capture devices disclosed herein are used to assess gene expression in urine samples (12 hour collection) collected from a subject four times over a two-week period. FIG. 10A depicts this gene expression data, and, notably, the level of gene expression (within each gene tested) is highly similar throughout the two-week experimental period. FIG. 10B depicts the data for three housekeeping genes over time. Of note, is a highly stable gene expression profile of each of these genes, thereby confirming accuracy of mRNA expression profiling when exosomes are captured using the devices disclosed herein.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "administering a blood test" include "instructing the administration of a blood test." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 3 mm" includes "3 mm."

What is claimed is:

1. A method of isolating vesicles from biological fluid, the method comprising:
   (a) obtaining a urine sample comprising said vesicles;
   (b) titrating said urine sample comprising said vesicles with a buffer solution comprising either phosphate buffered saline or HEPES to adjust the salt concentration of the urine sample comprising said vesicles to between 200 mM and 900 mM;
   (c) adjusting the pH of the urine sample comprising said vesicles to between about pH 6 and pH 9; and
   (d) passing said urine sample comprising said vesicles through a vesicle-capture material, said vesicle-capture material comprising glass-like materials, to produce a supernatant, wherein the vesicles from said urine sample are captured on or in said vesicle-capture material, wherein said titrating and said adjusting the pH of the urine sample comprising said vesicles is performed prior to passing said urine sample comprising said vesicles through the vesicle-capture material.

2. The method of claim 1, wherein the supernatant is discarded.

3. The method of claim 1, further comprising re-passing the supernatant through the vesicle-capture material.

4. The method of claim 1, wherein said salt concentration is between 200 mM and 600 mM.

5. The method of claim 1, wherein the salt concentration is based on the concentration of monovalent cations in the sample.

6. The method of claim 1, wherein the salt concentration that is adjusted is the concentration of monovalent cations.

7. The method of claim 1, wherein the said glass-like material comprises at least a first layer and a second layer of glass fiber.

8. The method of claim 7, wherein the said glass-like material is configured to have a greater than 50% retention rate for particles having a diameter of from 0.6 microns to 1.5 microns in diameter.

9. The method of claim 1, wherein the vesicles are selected from the group consisting of exosomes, vesicles, and other circulating membrane bound nucleic acid and/or protein-containing structures.

10. The method of claim 1, wherein the vesicles contain a biomarker selected from the group consisting of mRNA, miRNA, rRNA, tRNA, and vRNA.

11. The method of claim 1, wherein the salt concentration of the urine sample is adjusted to between about 200 mM and 600 mM.

12. The method of claim 1, wherein said adjusting the pH of the urine sample is performed prior to passing said urine sample through the vesicle-capture material.

13. The method of claim 12, wherein the salt concentration of the urine sample is adjusted to between about 200 mM and 600 mM.

* * * * *

UNITED STATES PATENT AND TRADEMARK OFFICE
CERTIFICATE OF CORRECTION

PATENT NO. : 10,697,001 B2
APPLICATION NO. : 15/456236
DATED : June 30, 2020
INVENTOR(S) : Masato Mitsuhashi et al.

It is certified that error appears in the above-identified patent and that said Letters Patent is hereby corrected as shown below:

On the Title Page

On Page 3, Column 1, Item (56), Line 4, under Other Publications, delete "pateints" and insert --patients--.

On Page 3, Column 1, Item (56), Line 4, under Other Publications, delete "symdrome," and insert --syndrome,--.

On Page 3, Column 1, Item (56), Line 21, under Other Publications, delete "namomembrane" and insert --nanomembrane--.

On Page 3, Column 2, Item (56), Line 18, under Other Publications, delete "Acquaporin" and insert --Aquaporin--.

On Page 3, Column 2, Item (56), Line 19, under Other Publications, delete "Archiv" and insert --Arhiv--.

On Page 3, Column 2, Item (56), Line 34, under Other Publications, delete "Willibrand" and insert --Willebrand--.

On Page 3, Column 2, Item (56), Line 68, under Other Publications, delete "Syndrom" and insert --Syndrome--.

On Page 3, Column 2, Item (56), Line 70, under Other Publications, delete "Tubuel-," and insert --Tubule-,--.

On Page 4, Column 1, Item (56), Line 24, under Other Publications, delete "Elesevier," and insert --Elsevier,--.

On Page 4, Column 1, Item (56), Line 26, under Other Publications, delete "Scientic," and insert Signed and Sealed this
Seventeenth Day of November, 2020

Andrei Iancu
*Director of the United States Patent and Trademark Office*

CERTIFICATE OF CORRECTION (continued)
U.S. Pat. No. 10,697,001 B2

--Scientific,--.

On Page 4, Column 1, Item (56), Lines 47-48, under Other Publications, delete "prespective," and insert --perspective,--.

On Page 4, Column 2, Item (56), Line 16, under Other Publications, delete "(PCT/US2011040076)." and insert --(PCT/US2011/040076).--.

On Page 4, Column 2, Item (56), Line 45, under Other Publications, delete "Keratinocy1e" and insert --Keratinocyte--.

On Page 4, Column 2, Item (56), Line 48, under Other Publications, delete "biotinylted" and insert --biotinylated--.

On Page 4, Column 2, Item (56), Line 51, under Other Publications, delete "Urnary" and insert --Urinary--.

On Page 4, Column 2, Item (56), Line 61, under Other Publications, delete "viscles" and insert --vesicles--.

On Page 4, Column 2, Item (56), Line 62, under Other Publications, delete "Immunocological" and insert --Immunological--.

On Page 5, Column 1, Item (56), Line 16, under Other Publications, delete "paitents" and insert --patients--.

On Page 5, Column 2, Item (56), Line 5, under Other Publications, delete "Cerviocovaginal" and insert --Cervicovaginal--.

On Page 5, Column 2, Item (56), Lines 9-10, under Other Publications, delete "diabetes," and insert --disease,--.

On Page 6, Column 1, Item (56), Line 32, under Other Publications, delete "ExomL" and insert --Exosomal--.

On Page 6, Column 1, Item (56), Line 38, under Other Publications, delete "primay" and insert --primary--.

On Page 6, Column 2, Item (56), Line 2, under Other Publications, delete "5-methylcyotsine" and insert --5-methylcytosine--.

On Page 6, Column 2, Item (56), Line 8, under Other Publications, delete "IFN-Y" and insert --IFN-γ--.

On Page 6, Column 2, Item (56), Line 17, under Other Publications, delete "nRNAs," and insert --mRNAs,--.

CERTIFICATE OF CORRECTION (continued)
U.S. Pat. No. 10,697,001 B2

On Page 6, Column 2, Item (56), under Other Publications, Line 28, delete "Physican" and insert --Physician--.

In the Specification

In Column 9, Line 32, delete "samples" and insert --samples.--.

In Column 14, Line 44, delete "myristolylated," and insert --myristoylated,--.

In Column 14, Line 47, delete "selenoylated," and insert --selenylated,--.

In Column 19, Line 47, delete "multiwell" and insert --multi-well--.

In Column 20, Line 14 (Approx.), delete "RPLPO" and insert --RPLP0--.

In Column 20, Line 31, delete "RPLPO)" and insert --RPLP0)--.